(12) United States Patent
Kato et al.

(10) Patent No.: US 9,360,431 B2
(45) Date of Patent: Jun. 7, 2016

(54) BLUE-COLORED GOLD NANOPARTICLES FOR IMMUNOLOGICAL MEASUREMENT, PROCESS FOR PRODUCTION OF SAME, AND MEASUREMENT METHOD USING SAME

(75) Inventors: Yuya Kato, Kanagawa (JP); Daisuke Ito, Kanagawa (JP); Yoshiko Kitani, Kanagawa (JP)

(73) Assignee: Tanaka Kikinzoku Kogyo K.K., Chiyoda-ku, Tokyo (JP)

( * ) Notice: Subject to any disclaimer, the term of this patent is extended or adjusted under 35 U.S.C. 154(b) by 0 days.

(21) Appl. No.: 13/883,213

(22) PCT Filed: Nov. 4, 2011

(86) PCT No.: PCT/JP2011/075519
§ 371 (c)(1),
(2), (4) Date: May 2, 2013

(87) PCT Pub. No.: WO2012/060456
PCT Pub. Date: May 10, 2012

(65) Prior Publication Data
US 2013/0224885 A1 Aug. 29, 2013

(30) Foreign Application Priority Data

Nov. 5, 2010 (JP) ................. 2010-248463

(51) Int. Cl.
| | | |
|---|---|---|
| G01N 33/543 | (2006.01) | |
| G01N 21/75 | (2006.01) | |
| G01N 33/58 | (2006.01) | |
| B22F 1/00 | (2006.01) | |

(Continued)

(52) U.S. Cl.
CPC .............. *G01N 21/75* (2013.01); *B22F 1/0025* (2013.01); *B22F 9/24* (2013.01); *B82Y 30/00* (2013.01);

(Continued)

(58) Field of Classification Search
CPC .......... G01N 33/54346; G01N 33/587; G01N 33/54353; G01N 2021/6441; B22F 9/24; B22F 1/0018; B22F 2301/255; B22F 2304/054; B22F 2304/056
USPC ....................................................... 436/525
See application file for complete search history.

(56) References Cited

U.S. PATENT DOCUMENTS

| | | | |
|---|---|---|---|
| 2007/0110671 A1* | 5/2007 | Chamberlin et al. | .......... 424/9.6 |
| 2009/0022765 A1 | 1/2009 | Chung | |
| 2010/0059726 A1 | 3/2010 | Jung | |

FOREIGN PATENT DOCUMENTS

| | | |
|---|---|---|
| JP | 2006-233316 | 9/2006 |
| JP | 2007-321232 | 12/2007 |

(Continued)

OTHER PUBLICATIONS

Xie et al. (Chem. Mater. 2007, 19, 2823-2830).*

(Continued)

*Primary Examiner* — Mark Shibuya
*Assistant Examiner* — Pensee Do
(74) *Attorney, Agent, or Firm* — Orrick Herrington & Sutcliffe, LLP

(57) ABSTRACT

Gold nanoparticles which comprises organic buffer containing a piperazine ring, gold, and an organic acid having reducing properties and which shows a blue color by visually view when it is dispersed as a colloidal solution, can be produced easily by conducting a nucleus formation step by reacting organic acid containing a piperazine ring with a solution of a first gold salt to form nucleus gold nanoparticles and a growth step by simultaneously adding and reacting a solution of a second gold salt and an organic acid having reducing properties with a solution of the nucleus gold nanoparticle to grow the nucleus gold nanoparticles. The produced gold nanoparticles can be used as labeling particles in an immunological measurement method.

14 Claims, 6 Drawing Sheets

(51) Int. Cl.
  *B22F 9/24* (2006.01)
  *B82Y 30/00* (2011.01)

(52) U.S. Cl.
  CPC ......... *G01N 33/585* (2013.01); *B22F 2301/255* (2013.01); *B22F 2304/054* (2013.01); *B22F 2304/056* (2013.01)

(56) References Cited

FOREIGN PATENT DOCUMENTS

| | | |
|---|---|---|
| JP | 2008-545884 | 12/2008 |
| JP | 2009-501786 | 1/2009 |
| JP | 2009-168495 | 7/2009 |
| JP | 2011-16778 | 1/2011 |
| JP | 2011-162837 | 8/2011 |

OTHER PUBLICATIONS

Office Action dated Aug. 28, 2014, issuing in counterpart CN Appln. No. 201180053388.6.

International Search Report for PCT/JP2011/075519, dated Jan. 31, 2011.

* cited by examiner

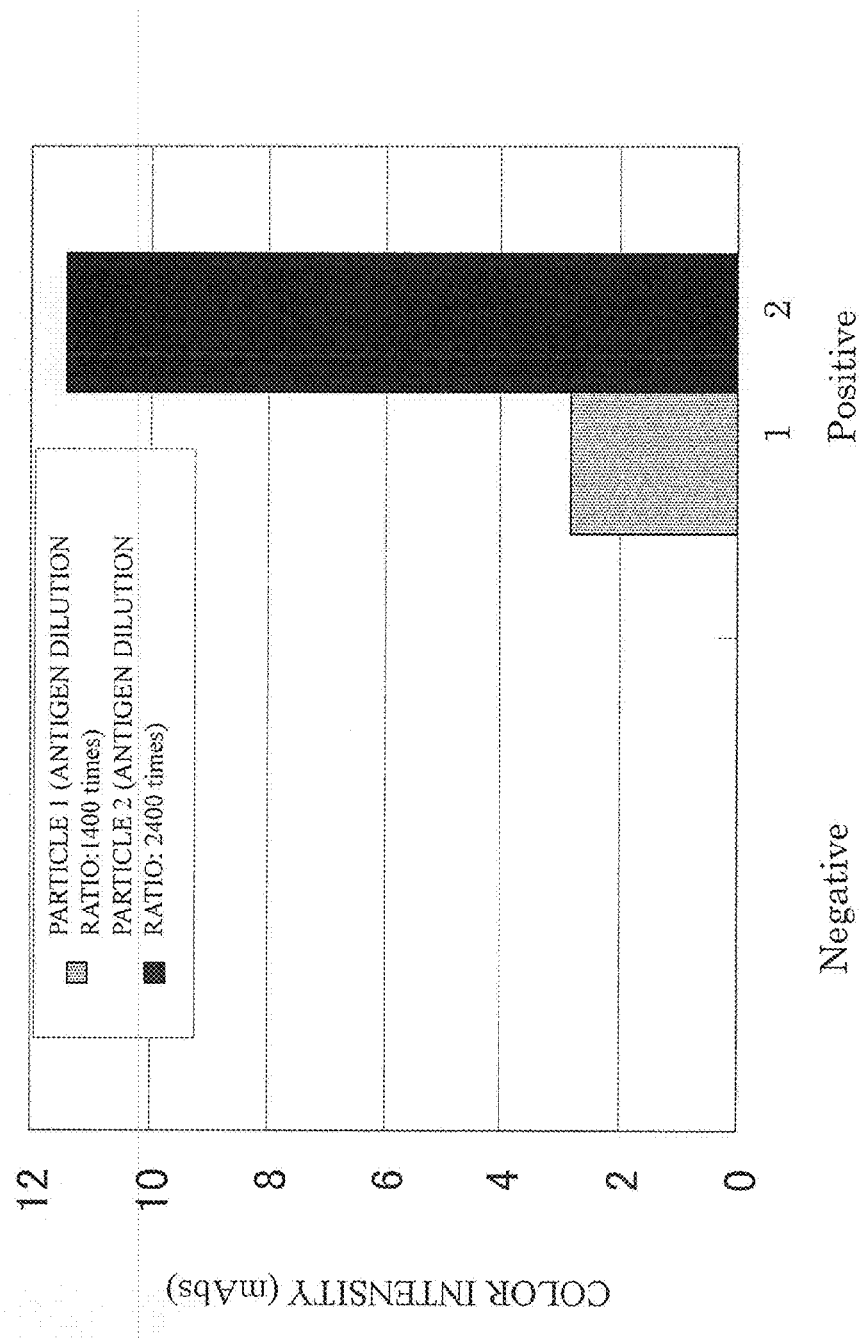

BLUE-COLORED GOLD NANOPARTICLES FOR IMMUNOLOGICAL MEASUREMENT, PROCESS FOR PRODUCTION OF SAME, AND MEASUREMENT METHOD USING SAME

TECHNICAL FIELD

The present invention relates to blue-colored gold nanoparticles and a colloidal solution of blue-colored gold nanoparticles, each having a highly vivid color developing property and at the same time, having stable durability and excellent distinguishability and useful as a labeling agent for immunological measurement or a protein stain. The present invention also relates to a method for producing the blue-colored gold nanoparticles of the present invention, and a test kit and a measuring method using the blue-colored gold nanoparticles. Moreover, the present invention relates to a labeling substance for immunological measurement in which the blue-colored gold nanoparticles of the present invention is used as a labeling substance in an immunological measurement system.

BACKGROUND ART

In recent years, immunochromatographic strip type immunoassay has become more important as a simple in-vitro diagnostic kit or portable diagnostic device for detecting an antigen in a sample solution by making use of the specific reactivity which an antibody has. In particular, simple multiplex analysis tools based on immunochromatography for analyzing the presence or absence of infection with pathogens such as influenza virus or bacteria have been under research and development.

Colloidal metal particles or latex particles have generally been used as an insoluble carrier to be used in an immunological measurement method. Latex particles need a cumbersome production step such as modification of a chemical functional group in order to firmly support a substance such as protein to be labeled. Therefore, colloidal gold particles capable of easily supporting a substance to be labeled and are produced conveniently at a low cost have been preferably used.

Although immunochromatographic test drugs which have labeled an antibody with an insoluble carrier have been used generally since they are easy to operate and need only a short time for the test, a line which can be observed when the test result is positive is not clear since they have generally lower sensitivity in comparison with EIA.

In order to overcome such a problem, various metal colloids having a higher sensitivity than conventional colloidal metal particles already put into practical use and are suitable as labeling agents for immunological measurement or protein staining agents are developed.

Patent Document 1 provides colloidal metal particles having an average particle size of from 50 to 150 nm obtained by supporting platinum on the surface of colloidal metal particles (average particle size: from 30 to 100 nm) since colloidal platinum particles do not develop color sufficiently due to small average particle size and are not suited for practical use in immunochromatography. The colloidal metal particles are prepared by reducing chloroauric acid in a solvent to form colloidal gold particles and then reducing chloroplatinic acid in the presence of the resulting colloidal gold particles (refer to Patent Document 1).

Patent Document 2 provides colloidal metal particles obtained by improving the above-mentioned colloidal metal particles and therefore having higher sensitivity. Namely, colloidal metal particles (average particle size: 30 to 100 nm) having platinum supported thereon which has an average particle size of 5 nm are provided. They are prepared in a production method wherein by adjusting, to a predetermined range, the amount of a reducing agent added in preparing colloidal metal particles in a medium and the amount of a reducing agent added in reducing and supporting platinum on the colloidal metal particles and wherein the medium does not substantially contain a protective colloid forming agent. Examples of such protective colloid forming agent include water soluble high-molecular substances such as PVA, PVP, and gelatin, surfactants, and high-molecular chelating agents (refer to Patent Document 2).

As another method for improving the sensitivity in immunological and immunocytological diagnostic test, a method of coating gold sol ultrafine particles with an alkanethiol (derivative) to impart the gold sol surface with certain hydrophobic-hydrophilic balance so as to prevent aggregation which is caused by a salt by which non-specific interaction between the gold sol surface and an exogenous protein (refer to Patent Document 3) is minimized is provided.

On the other hand, in vitro diagnostics for pregnancy diagnosis, red-colored spherical colloidal gold particles already put on the market have been improved to exhibit higher sensitivity. Colloidal gold is required to have a particle size suited for an intended use; have a sharp particle size distribution; and have a uniformly spherical shape so that a production process of it is under development.

Patent Document 4 includes a nucleus formation stage of adding a first reducing agent (citrate) to a solution of a first gold salt to form colloidal nucleus particles (average particle size: from 12 to 17 nm) and a growth stage of simultaneously adding, to the solution of the colloidal nucleus particles, a second gold salt and a second reducing agent (ascorbate) to grow a colloidal nucleus. This growth stage is conducted at least once. The average particle size of the colloidal gold particles is 17 nm or greater and less than 55 nm in the first growth stage; 55 nm or greater and less than 110 nm in the second growth stage; and from 110 to 220 nm in the third growth stage. The standard deviation of the particle diameter is within 10% (refer to Patent document 4).

In the case of testing only one item such as a pregnancy test kit for finding whether pregnancy or not, it is only necessary to use one labeling agent in visual judgment. Recently, a multiplex test should be conducted when it is necessary to identify a causative virus as in a virus test in cold-like infections or respiratory infections. Thus, various test systems have been developed with a view to easing the burden of patients and health care workers.

For example, although there is a known lateral flow type immunoassay capable of detecting a plurality of viruses (rotavirus, calcivirus, coronavirus, adenovirus, enterovirus, and the like) by using one test tool, the assay has the problem that a plurality of detection lines tend to lead to erroneous visual judgment.

In the test of a virus in respiratory infections by using immunochromatography, a testing method including pretreating a specimen such as nasal discharge, sputum or a swab from the nasal cavity with a specimen treatment solution to prepare a test sample suited for the test of a plurality of respiratory infections and analyzing respective portions of the resulting test sample by using a plurality of test tools such as a first test tool (for example, testing an influenza virus infection) and a second test tool (for example, testing an adenovirus infection or an RS virus infection) (refer to Patent Document 5) has been developed.

Further, a measurement method including immunochromatography having a high ability of judging with labeled antibody particles having an arbitrary color and capable of simultaneously measuring two or more measurement objects by using two or more labeled antibody particles has been developed. More specifically, hCG and LH are measured simultaneously by using a luminescent dye such as TRITC (absorption maximum: about 550 nm, red) and FITC (absorption maximum: about 500 nm, orange) (refer to Patent Document 6).

When multiplex tests are conducted simultaneously through visual judgment by using one test tool and labeling agents or protein staining agents used are of the same color or similarcolor, there is a possibility of causing misjudgment or wrong diagnosis. In order to prevent misjudgment or wrong diagnosis by visual judgment, it is desired to conduct visual judgment by using labeling agents or protein staining agents of highly distinguishable colors.

When two colors are present, their distinguishability differs with the colors used in combination. Since a red color and a blue color can be highly distinguished from each other by visually view, they are used for various distinguishing purposes as can be seen in indications for distinguishing between male and female or indications for distinguishing between hot water (red) and water (blue). Colloidal gold particles which have been conventionally put into practical use are red-colored spherical particles. If blue-colored colloidal gold particles different in color, in other words, highly distinguishable from red color are used as a labeling agent or protein staining agent, misjudgment or wrong diagnosis through visual judgment is presumed to decrease markedly. However, blue-colored colloidal gold particles have not yet been put into practical use.

In patent Documents 7 to 9, metal nanoparticles having light absorption wavelength properties varied by changing the size, pattern, structure/shape or the like of metal nanoparticles are described.

According to Patent Documents 7 and 8, blue-colored gold nanoparticles have a structure/shape of gold nanoshells, nanorods, nanotubes, or nanoprism particles; the gold nanoparticles are produced by (1) adding a reducing agent to a yellow-colored silver nanoparticle solution (containing a protecting agent such as polyvinylpyrrolidone or ethylene glycol) and then, refluxing the resulting mixture at about 100° C., (2) pouring a gold salt solution in the reaction mixture thus refluxed to react them, and (3) after cooling to normal temperature, the reaction mixture is filtered through a 0.2 μm microfilter; and the gold nanoparticles thus obtained are made of gold (gold nanoshell) only at the surface layer thereof. According to these documents, gold nanorods, gold nanotubes, or gold nanoprisms are obtained by using a surfactant such as hexadecyltrimethylammonium bromide (bromide) ($C_6TAB$) in formation of gold nanoparticles. These documents do not include a definite description on the size of the particles. They include a description on the use of them as pigment for cosmetics but do not include a description on the use of them as a labeling agent or protein staining agent in immunoassay (refer to Patent Documents 7 and 8).

Patent Document 9 describes rod-like gold nanoparticles obtained by reducing a gold ion with a reducing agent (an amine) in an aqueous solution containing $Cl_6TAB$ (a surfactant of an ammonium salt). The aspect ratio (long axis/short axis) of the gold nanoparticles can be controlled by regulating a mixing ratio of the amine and the ammonium salt used in combination. By doing so, gold nanorods having an aspect ratio of from 2 to 11 and an absorption wavelength peak area of from 658 to 1200 nm are obtained. According to the description, these gold nanorods can be used as a test drug (refer to Patent Document 9).

Since the gold nanoparticles thus obtained contain $C_{16}TAB$ as a surfactant, they are not suited for directly supporting (modifying) with protein such as detection antibody. Since it needs a cumbersome operation such as removal or substitution of the surfactant, it is not preferred as a labeling substance for a protein to be used as a test drug in the immunological measurement method. In addition, they are not preferred from the standpoint of handling because $C_6TAB$ has toxicity.

Non-patent Document 1 describes a colloid of stick-shaped gold nanocrystals exhibiting a bluish green color. The stick-shaped gold naocrystals have a complex three-dimensional structure; have from one to eight protrusions; and have a crystal size, including the protrusion, of from 30 to 50 nm (protrusion length of from about 15 to 25 nm and a width of about 8 nm). The three-dimensional branch-shaped gold nanocrystals are obtained in a high yield (92%) by reacting an aqueous solution of chloroauric acid and an organic acid (HEPES, HEPPSO, PIPES, or the like) which is a Good's buffer component at room temperature (refer to Non-patent Document 1).

However, the colloid of branch-shaped nanocrystals obtained in Non-patent Document 1 and exhibiting a bluish green color has a crystal size of from 30 to 50 nm, which is not a desired size. Therefore, even if it is used as an immunochromatographic diagnostic agent, insufficient color development prevents smooth visual judgment.

As can be seen in the related art documents, a colloid of gold nanocrystals exhibiting a bluish green color is not suited as a labeling carrier of an immunochromatographic diagnostic agent since the colloidal particle size is as relatively small as from about 30 to 50 nm. In addition, so-called multipod-shaped, branch-shaped, or confeito-shaped ones often use a shape stabilizer and the shape stabilizer makes it difficult to achieve direct modification of gold nanoparticles with a protein.

PRIOR ART DOCUMENTS

Patent Documents

Patent Document 1: JP-A-2003-262638
Patent Document 2: JP-A-2005-233744
Patent Document 3: JP-A-6-116602
Patent Document 4: JP-A-2007-321232
Patent Document 5: JP-A-2008-164403
Patent Document 6: JP-A-10-132817
Patent Document 7: JP-A-2008-545884
Patent Document 8: JP-A-2009-501786
Patent Document 9: JP-A-2006-118036

Non-Patent Documents

Non-Patent Document 1: Chem. Mater. 2007, 19, 2823-2830
Non-Patent Document 2: Langmuir 2005, 21, 2012-2016
Non-Patent Document 3: J. Phys. Chem. B 2006, 110, 19291-19294
Non-Patent Document 4: Nano Lett. 2006, 6, 683-688

SUMMARY OF THE INVENTION

Problems to be Solved by the Invention

An object of the present invention is to provide blue-colored gold nanoparticles, a colloidal solution of blue-colored gold nanoparticles obtained by dispersing the gold nanoparticles in a medium, and blue-colored gold nanoparticles exhibiting a highly vivid blue color with visually view, excellent in quality stability, storage stability and distinguishability, useful as a labeling agent for immunological measurement or protein staining agent, and easily distinguishable by a difference in color from a conventional red color; and to overcome the problem relating to the production method of the blue-colored gold nanoparticles, a test kit having enhanced measurement accuracy by using the blue-colored gold nanoparticles, and the measurement method using the test kit.

Blue-colored gold nanoparticles in Non-patent Documents 1 to 3 used above as reference are not suited as a carrier for immunochromatographic diagnostic agent because of the following two problems:

1. These blue-colored gold nanoparticles have a size which is not suited for immunological measurement. The particle size suited for immunochromatography reagent is from about 40 to 100 nm in terms of average particle size. According to Non-patent Document 1, the particle size is about 30 nm.

2. They contain a shape stabilizer. The three-dimensional stick-shaped gold nanoparticles described in Non-patent Document 2 to 4 contain a shape stabilizer in order to control their shape. The shape stabilizer prevents direct modification of gold nanoparticles with a protein.

When a multiplex test is carried out and conventional red-colored gold nanoparticles and colored latex particles are used for the simultaneous multiplex measurement, it is difficult to select, in immunochromatography, an immunochromatographic carrier having a pore size suited for both particles since the gold nanoparticles and latex particles are different in the particle size (the latex particles generally employed have a greater size than the gold nanoparticles). Therefore, it is required to use, as a labeling substance, two kinds of colloidal gold particles which are different in color; capable of easily supporting a substance to be labeled such as protein; and inexpensive.

In order to overcome the above-mentioned problems, the inventors of the present invention have succeeded in providing blue-colored gold nanoparticles suited for a carrier of an immunochromatographic diagnostic agent, more specifically, blue-colored gold nanoparticles usable for a multiplex detection reagent in multiplex detection by immunochromatography by increasing the size of the particles in order to make it suited for immunological measurement and by selecting a shape stabilizer permitting direct modification of gold nanoparticles with a protein.

Means for Solving the Problems

The present invention provides blue-colored gold nanoparticles suited for immunological measurement, permitting easy modification of the gold nanoparticles with a protein and at the same time, most suited as a multiplex detection reagent.

Described specifically, the blue-colored gold nanoparticles of the present invention are composed of organic acid containing a piperazine ring (such as HEPES) which is a Good's buffer component, Au (gold) and an organic acid having reducing properties (such as ascorbic acid and citric acid); exhibits a blue color when viewed visually; and has a confeito-like shape.

The blue-colored gold nanoparticles of the present invention have an average particle size of from 20 to 200 nm, preferably from 40 to 180 nm from the standpoint of color vividness, stable durability, and stable durability of a colloid, typically most preferably from 50 to 120 nm from the various practical standpoints including marked distinguishability in a test. The most appropriate range is from 60 to 100 nm. The blue-colored gold nanoparticles have a feature of a blue color with visual view in liquid wherein the blue-colored gold nanoparticles are dispersed as colloid.

The term "average particle size" as used in the present invention means a value determined by including a nucleus protruding portion of blue-colored cold nanoparticles which will be described later. In the blue-colored gold nanoparticles of the present invention, the nucleus protruding portion has a length of preferably from 5 to 50 nm. The number of protrusions is four or more per nucleus.

In an aqueous colloidal solution containing the blue-colored gold nanoparticles according to the present invention, the colloidal gold particles have an average particle size of from 20 to 200 nm, preferably from 40 to 180 nm, usually most preferably from 50 to 120 nm, most appropriately from 60 to 100 nm. Its average particle nucleus size is from 20 to 60 nm. The aqueous colloidal solution containing the blue-colored gold nanoparticles according to the present invention is characterized by that it has a maximum absorption wavelength in a range of from 570 to 750 nm in an ultraviolet visible absorption spectrum. By using the gold nanoparticles contained in the aqueous colloidal gold solution of the present invention as a labeling substance in immunochromatography, detection with a blue color highly distinguishable from a red color is possible. This makes it possible to conduct immunochromatography measurement with reducing wrong diagnosis cases in the simultaneous multiplex detection. It is to be noted that the term colloidal solution of the blue-colored gold nanoparticles according to the present invention means a dispersion of fine particles with a nanosize (nm), particularly gold nanoparticles, in a solvent such as water. In short, the present invention has succeeded in providing blue-colored nanoparticles, a colloidal solution of blue-colored gold nanoparticles, a production method thereof, and confeito-shaped blue-colored gold nanoparticles suited for immunological measurement; permitting easy modification of blue-colored gold nanoparticles with a protein; and at the same time, most suited as a multiplex detection reagent.

The present invention provides blue-colored gold nanoparticles and production method and using method of them. The gold nanoparticles of the present invention have characteristics as follows:

(a) The first feature of the present invention is blue-colored gold nanoparticles comprising gold nanoparticles having an average particle size of from 20 to 200 nm;

(b) The second feature of the present invention is the blue-colored gold nanoparticles according to (a), wherein the maximum absorption wavelength in ultraviolet visible absorption spectra falls within a range of from 570 to 800 nm;

(c) The third feature of the present invention is the blue-colored gold nanoparticles according to (a) or (b), wherein the gold nanoparticles are graft-shaped particles, multipod-shaped particles, or confeito-shaped particles having a three-dimensional protrusion;

(d) The fourth feature of the present invention is the blue-colored gold nanoparticles according to any one of (a) to (c), obtained by growing the periphery of the nucleus composed of gold nanoparticles; and (e) The fifth feature of the present invention is the blue-colored gold nanoparticles according to any one of (a) to (d), having an average particle nucleus size of from 20 to 60 nm, an average particle size of from 50 to 120 nm, four or more protrusions per nucleus, and a protrusion length of from 5 to 50 nm.

The colloid wherein the gold nanoparticles of the present invention are dispersed in a medium such as water has characteristics as follows:

(f) The sixth feature of the present invention is a colloidal solution of blue-colored gold nanoparticles, comprising the blue-colored gold nanoparticles as described in (a); organic acid containing a piperazine ring which is a Good's buffer component; and an organic acid having reducing properties and is dispersed as a colloidal solution.

The production methods for specifically gold nanoparticles of the present invention has characteristics as follows:

(g) The seventh feature of the present invention is a method for producing blue-colored gold nanoparticles, comprising a nucleus formation step by reacting organic acid containing a piperazine ring which is a Good's buffer component with a solution of a first gold salt to form nucleus gold nanoparticles and a growth step by simultaneously adding and reacting a solution of a second gold salt and an organic acid having reducing properties with a solution of the nucleus gold nanoparticle to grow the nucleus gold nanoparticles;

(h) The eighth feature of the present invention is the method for producing blue-colored gold nanoparticles according to (g), wherein the growth step is conducted at a reaction temperature of 10° C. or greater and less than 40° C.;

(i) The ninth feature of the present invention is the method for producing blue-colored gold nanoparticles according to (g) or (h), wherein the organic acid in the growth step has a concentration of from 0.075 to 0.15 mM;

(j) The tenth feature of the present invention is the method for producing blue-colored gold nanoparticles according to (i), wherein the organic acid containing piperazine ring which is a Good's buffer component is one or more organic acids selected from the group consisting of 2-[4-(2-hydroxyethyl)-1-piperazinyl]ethanesulfonic acid, 4-(2-hydroxyethyl)-1-piperazinepropanesulfonic acid, 4-(2-hydroxyethyl)piperazine-1-(2-hydroxypropane-3-sulfonic acid), piperazine-1,4-bis(2-ethanesulfonic acid), 3-[4-(2-hydroxyethyl)-1-piperazinyl]propanesulfonic acid, and piperazine-1,4-bis(2-hydroxy-3-propanesulfonic acid);

(k) The eleventh feature of the present invention is the method for producing blue-colored gold nanoparticles according to (g), wherein the organic acid having reducing properties is one or more organic acids selected from the group consisting of tartaric acid, tartrates, tannic acid, tannates, ascorbic acid, ascorbates, citric acid, and citrates; and (l) The twelfth feature of the present invention is the method for producing blue-colored gold nanoparticles according to (g), wherein in the growth step, the organic acid containing a piperazine ring which is a Good's buffer component is used in combination with the organic acid having reducing properties.

Next, the present invention, specifically, as the labeling substance for immunological measurement has characteristics as follows:

(m) The thirteenth feature of the present invention is a labeling substance for immunological measurement, comprising the blue-colored gold nanoparticles as described in any one of (a) to (e);

(n) The fourteenth feature of the present invention is the labeling substance for immunological measurement according to (m), comprising at least two kinds of gold nanoparticles different in shape;

(o) The fifteenth feature of the present invention is the labeling substance for immunological measurement according to (n), which comprises at least two kinds of gold nanoparticles of different shapes which are spherical gold nanoparticles and graft-shaped, multipod-shaped, or confeito-shaped gold nanoparticles having a three-dimensional protrusion; and (p) The sixteenth feature of the present invention is an immunological measurement method using the blue-colored gold nanoparticles as described in any one of (a) to (e) as a labeling substance.

The problems of the present invention can be overcome by employing the above-mentioned constitutions of the present invention.

Effect of the Invention

Since the blue-colored gold nanoparticles of the present invention have an average particle size of from 20 to 200 nm; preferably from 40 to 180 nm; usually most preferably from 50 to 120 nm; and most appropriately from 60 to 100 nm, the blue-colored gold nanoparticles can provide a particle size which is most suited for an immunochromatographic diagnostic agent.

Using in combination with spherical red-colored gold nanoparticles or the like enables preparation of an immunochromatographic diagnostic agent having two or more judgment lines. This prevents wrong diagnosis or misjudgment since visual judgment can be made easily and precisely in a multiplex test.

Moreover, the blue-colored gold nanoparticles of the present invention can be easily modified with a protein so that they enable precise judgment of the results without causing deterioration in sensitivity. They are therefore excellent in the performance as an immunochromatographic diagnostic agent.

Furthermore, an immunochromatographic diagnostic agent prepared from the blue-colored gold nanoparticles of the present invention is more inexpensive than those prepared from particles obtained by another method.

BRIEF DESCRIPTION OF THE DRAWINGS

FIG. 6 shows the comparison in detection sensitivity when the blue-colored gold nanoparticles of the present invention are used as an immunochromatographic reagent.

MODE FOR CARRYING OUT THE INVENTION

Figure 1A:
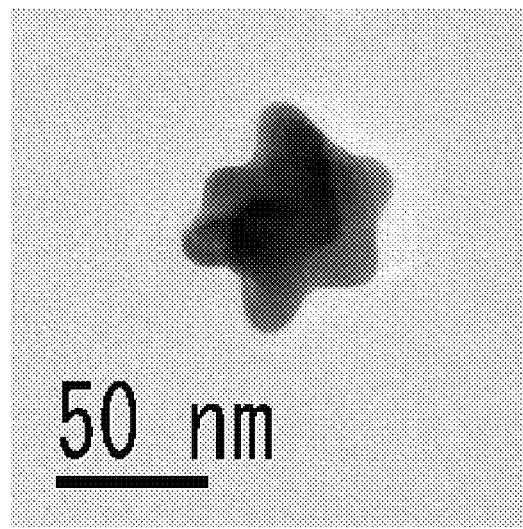
FIG. 1A is a transmission electron microscope image showing the shape and rough size of one example of the blue-colored gold nanoparticles of the present invention.

As the blue-colored gold nanoparticles of the present invention, although it is ideal to produce, those having a large average particle size in one step, it is rational to form particles with a predetermined size first and then, conduct a growth step to obtain particles with a larger particle size. The blue-colored gold nanoparticles of the present invention are composed of gold nanoparticles having an average particle size of from 20 to 200 nm. The average particle size of colloidal gold particles of a colloidal solution obtained by dispersing the gold nanoparticles of the present invention in a medium is from 20 to 200 nm; preferably from 40 to 180 nm; usually most preferably from 50 to 120 nm; and the most appropriate range is from 60 to 100 nm. From various standpoints in practical use such as marked distinguishability in a test, the gold nanoparticles have preferably a sharp particle size distribution and have a uniform confeito-like shape. The average particle size can be determined typically by gravimetric light scattering (determined from the precipitation rate of colloidal particles rotated, as in a sol, at from 14000 to 5530000×g and treated in an ultracentrifuge). In the present invention, a projected area diameter of 100 particles selected at random from a projection photograph taken by a transmission electron microscope (TEM, "JEM-2010", product of JEOL, Ltd.) is measured and then, based on the average value, an average particle diameter (average particle size) is determined.

When the X-axis (for example, size of gold nanoparticles) and the Y axis (for example, number fraction) are set to make a particle size distribution of the gold nanoparticles and a distribution curve of average particles is plotted along them, the apex of the distribution curve of the gold nanoparticles of the present invention substantially belongs to a particle size ranging from typically from 40 to 120 nm, preferably from 50 to 110 nm, more preferably from 60 to 100 nm. This reveals that this distribution curve is relatively narrow, which means that many nanoparticles have a particle size approximating to each other and thus have a uniform particle size. It is expected that the nanoparticles exhibit stable and highly reliable behaviors and suppress generation of an error span due to foreign matters mixed therein.

Quantitatively, a total weight of the gold nanoparticles belonging to the range of from 20 to 200 nm is usually 40% or greater, preferably 60% or greater, more preferably 80 wt % or greater. The remaining portion is composed of particles which have remained without growing, spherical ones, and unreacted residue.

The gold nanoparticles of the present invention are so-called confeito-shaped nanoparticles having a nucleus and a three-dimensional protrusion. Those having any average particle size within a range of from 20 to 200 nm can be obtained by changing the operation of the production method. In use as labeling particles, those having an average particle size falling within a range of from 50 to 120 nm, preferably within a range of from about 55 to 100 nm are excellent in enhancing the accuracy of visual judgment based on a particular color of the labeling particles.

These confeito-shaped particles have preferably a plurality of three-dimensional protrusions. The term average particle size as used herein means a value determined including the nucleus protrusion. The gold nanoparticles of the present invention have from about 1 to 20 protrusions, preferably from about 4 to 10 protrusions per nucleus. The length of each protrusion is typically from about 5 to 50 nm. It is very difficult to determine the number or length of these protrusions in advance, because they depend on the growth of the nuclei.

Figure 1B:
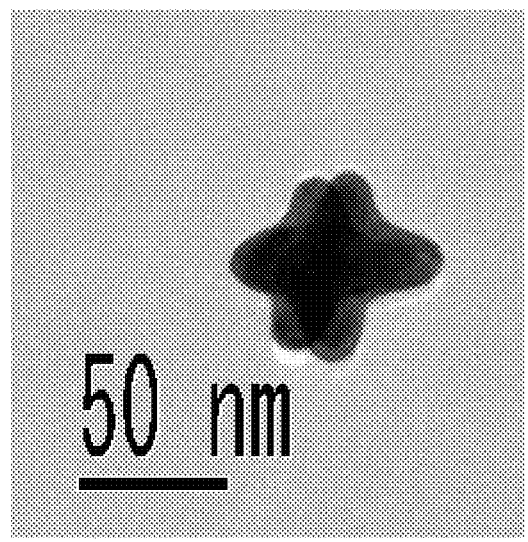
FIG. 1B is a transmission electron microscope image showing the shape and rough size of another example of the blue-colored gold nanoparticles of the present invention.

The gold nanoparticles and colloidal gold nanoparticles having a three-dimensional protrusion on the nucleus thereof are collectively called graft-shaped, multipod-shaped, or confeito-shaped gold nanoparticles and colloidal gold nanoparticles, respectively. As so-called gold nanoparticles and colloidal gold nanoparticles, there may be various structures having a three-dimensional protrusion and called by a known name such as nanocubes, nanorods, nanopods, star-shaped gold nanoparticles, or graft-shaped gold nanoparticles having, as shown in FIGS. 1A and 1B, a nucleus from which a stick-shaped protrusion has grown three-dimensionally. The colloidal gold nanoparticles developing a vivid blue color have a shape or structure analogous to that of a tetrapod used for breakwater. Therefore, the term is employed, the colloidal gold nanoparticles having one branch grown as a graft are called "monopod" and they may have various shapes such as "dipod", "tripod", "tetrapod", and "pentapod" with an increase in the number of branches. In the present invention, the number of protrusions per nucleus is preferably relatively large so that such shapes are collectively called "multipod".

The multipod-shaped colloidal gold nanoparticles or confeito-shaped colloidal gold nanoparticles according to the present invention exhibit a color, depending on their spreading manner, in comparison with conventional spherical colloidal gold particles exhibiting a red color. This enables a colloidal gold nanoparticle solution to exhibit various colors including blue.

Described specifically, as gold nanoparticles which are typical blue-colored gold nanoparticles of the present invention of graft-shaped, multipod-shaped, or confeito-shaped gold nanoparticles having a three-dimensional protrusion, gold nanoparticles having a shape as shown in FIG. 1A or 1B are shown as one example. These gold nanoparticles have, at the center portion thereof, a so-called nucleus and a protrusion or branch has grown as a graft on the nucleus. Since the growth starting point of the graft is in close contact with the nucleus, they look like multipod-shaped gold nanoparticles or confeito-shaped gold nanoparticles having a protrusion and a nucleus integrated with each other.

Examples of the gold nanoparticles in FIGS. 1A and 1B specifically show the example of blue-colored gold nanoparticles having a size of about 50 nm. More specifically, the gold nanoparticles shown in FIGS. 1A and 1B have an average particle size (DLS) of 66.5 nm and a maximum absorption wavelength of about 610 nm. In addition, according to the measurement through TEM observation, the gold nanoparticles have an average outer diameter of 62.2 nm, an average nucleus diameter of 35.7 nm, an average protrusion length of 13.2 nm, and a protrusion angle of about 50 degrees. They have an AR (aspect ratio) of 1 or greater. It is needless to say that the average outer diameter, average nucleus diameter, average protrusion length, and protrusion angle of the gold nanoparticles of the present invention can be changed arbitrarily in consideration of a predetermined product different in color.

In the present invention including Examples, the wavelength was measured in the following manner. The wavelength was measured using an ultraviolet visible absorption spectrometer (name of the spectrometer: "UV-2550", product of Shimadzu Corporation). It was measured under the following conditions: a quartz cell: 10 mm, wavelength: from 800 to 200 nm, and a band width: 0.5 nm.

The blue-colored gold nanoparticles and blue-colored colloidal gold nanoparticles are effective for the development of a multiplex diagnostic reagent. When there is a plurality of judgment lines, they can remove the possibility of wrong diagnosis upon visual judgment. Gold nanoparticles to be used as an immunological measurement labeling substance in such a multiplex diagnostic reagent are an immunological measurement labeling substance characterized by that they are composed of at least two kinds of gold nanoparticles different in shapes. More specifically, an immunological measurement labeling substance composed of at least two kinds of spherical red-colored gold nanoparticles and graft-shaped, multipod-shaped, or confeito-shaped blue-colored gold nanoparticles having a three-dimensional protrusion is suitable.

The gold nanoparticles of the present invention to be used as an immunological measurement labeling substance in a multiplex diagnostic reagent include, for example, a mixture (which will hereinafter be called "mixture-type gold nanoparticle labeling substance") of two kinds or three kinds of gold nanoparticles which are different in shape, for example, a mixture of spherical gold nanoparticles and gold nanoparticles having a three-dimensional protrusion. In this case, when the grain size distribution is analyzed by shape, the mixture type may form a distribution curve with two apexes, that is, a particle size distribution curve formed by the spherical gold nanoparticles and a particle size distribution formed by the gold nanoparticles having a three-dimensional protrusion. It is needless to say that in the case of a mixture of gold nanoparticles having three kinds of shapes different from each other, a particle size distribution curve having three apexes can be drawn. In the present invention, if the particle size distribution of at least two kinds of metal nanoparticles is analyzed without paying attention to a difference in shape, the average particle size inevitably falls within a relatively wide range of from 20 to 220 nm since gold nanoparticles having a relatively small average particle size and gold nanoparticles having a relatively large average particle size are present as a mixture. Anyway, when each particle size distribution curve forms a sharp peak, measurement accuracy can be enhanced, since it means that the amount of predetermined gold nanoparticles is larger. A detailed example of this mixture-type gold nanoparticle labeling substance will be described below.

The state of the "mixture-type gold nanoparticle labeling substance" of the present invention is described in detail. When the mixture-type gold nanoparticles of the present invention is recognized as two kinds and for example, one are spherical gold nanoparticles and the other are gold nanoparticles having a three-dimensional protrusion, a mixture is presumed to contain these two kinds of particles at a mass % ranging from 10:90 to 90:10 with taking into consideration of a detection sensitivity of label. It means that when the amount of the spherical gold nanoparticles is 40 mass %, the amount of the gold nanoparticles having a three-dimensional protrusion is 60 mass %. It is needless to say that the calculation is made with eliminating substances, other than predetermined ones, such as unreacted substances, nanoparticles which have remained without growing, and impurities.

For example, the spherical gold nanoparticles constituting this mixture-type gold nanoparticle labeling substance are relatively large particles having an average particle size of from 20 to 220 nm, preferably from 30 to 200 nm, and more preferably from about 40 to 150 nm. With regard to the gold nanoparticles having a three-dimensional protrusion, those having an average particle size of from about 20 to 200 nm may be present in the mixture. In order to enhance color vividness, color stability for long hours, stability of colloid, labeling accuracy, and reliability, the average particle size is preferably from 40 to 180 nm; usually most preferably from 50 to 120 nm; and the most appropriate range is from 60 to 100 nm.

The mixture-type gold nanoparticle labeling substance can be obtained, for example, by a simple method of mixing spherical gold nanoparticle labeling substance which has been prepared in advance and has a predetermined average particle size with a gold nanoparticle labeling substance having a three-dimensional protrusion at a predetermined ratio.

The immunological measurement labeling substance which is the mixture-type gold nanoparticle labeling substance of the present invention and composed of at least two kinds of gold nanoparticles which are different in shape contains at least two kinds gold nanoparticles to be used as a labeling substance constituting a labeling reagent which modifies a detector substance having a binding ability with a target substance in an immunological measurement system and labels through binding with the target substance, wherein 1) the two kinds of gold nanoparticles each have an average particle size of from 20 to 220 nm, and 2) one of the two kinds of gold nanoparticles is spherical and the other one has at least four three-dimensional protrusions.

When such a mixture-type gold nanoparticle labeling substance is used, various antigens can be discriminated clearly by a difference in color such as red and blue. Therefore, it can ease the burden on the test and simplify the test operation in the medical front. As a result, it can markedly improve its usefulness.

The colloidal gold particles of the present invention exhibit a blue color when they are viewed visually. It means that a colloidal gold solution obtained by dispersing colloidal gold particles in a solvent such as water exhibits a blue color or a color analogous to a blue color such as bluish green or bluish violet with visually view. More specifically, it means that the hue of the solution specified by the Munsell color system is from 3P to 1P, 10PB to 1PB, 10B to 1B, 10BG to 1BG, or 10G to 8G. Of these, the hue from 10PB to 1PB, from 10B to 1B, or from 10BG to 1BG is preferable in view of distinguishability from a red color. With regard to the colorimetry, a quartz cell (light path length: about 10 mm) used for spectrophotometric measurement is filled with the colloidal solution; the color tone of it is confirmed visually on a white background (white drawing paper); and then, the color hue is evaluated based on a commercially available Munsell book of color.

The method for producing gold nanoparticles according to the present invention includes a nucleus formation stage wherein a first gold salt in an aqueous solution is reduced with a first reducing agent into confeito-shaped nucleus gold nanoparticles and a growth stage wherein a second gold salt and a second reducing agent are added simultaneously dropwise to grow the nucleus gold nanoparticles into confeito-shaped gold nanoparticles having a greater size. The growth stage may be conducted at least once.

In order to form confeito-shaped gold nanoparticles having a longer protrusion in the growth stage, a mixture of the second reducing agent and the first reducing agent, namely, organic acid containing a piperazine ring which is a Good's buffer component is used.

The amount of the first reducing gent used in combination with the second reducing agent is almost equal to that of the second reducing agent, depending on the concentration of the second reducing agent to be used in the growth stage. Namely, the concentration of the first reducing agent for use is adjusted to be within a range of from 0.01 to 100 mM in an aqueous solution for growing the nucleus gold nanoparticles in the growth stage.

In order to analyze the behavior of the chemical species of the blue-colored gold nanoparticles, as one mode, particles corresponding to the nucleus particles before the growth reaction are called "Particle 1" and a solution of "Particle 1" is prepared by mixing 0.43 mM $AuCl_4$ and 39.0 mM HEPES. Particles corresponding to particles which have grown as a result of the growing reaction are called "Particle 2" and a solution of "Particle 2" is prepared by mixing 0.05 mM $AuCl_4$, 0.82 mM HEPES, and 0.10 mM ascorbic acid. The behavior of the resulting solutions is analyzed.

Figure 2A:
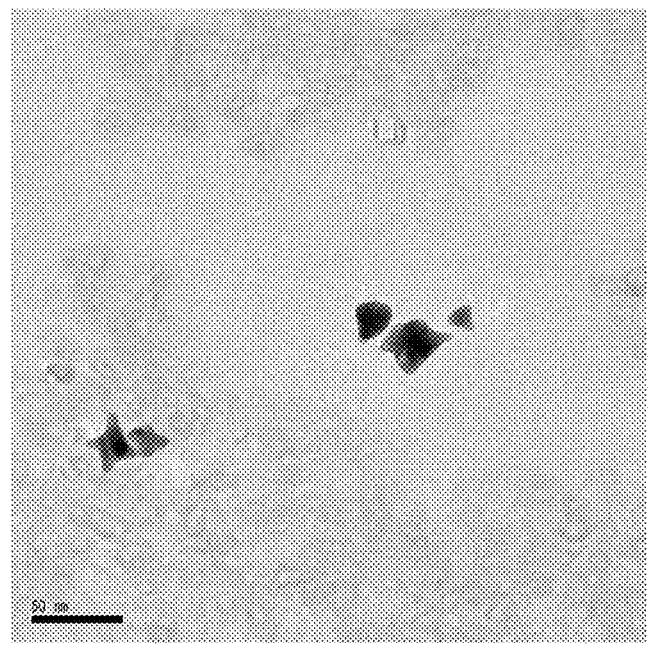
FIG. 2A is a transmission electron microscope image of one example of the blue-colored gold nanoparticles of the present invention before growth.
Figure 2B:
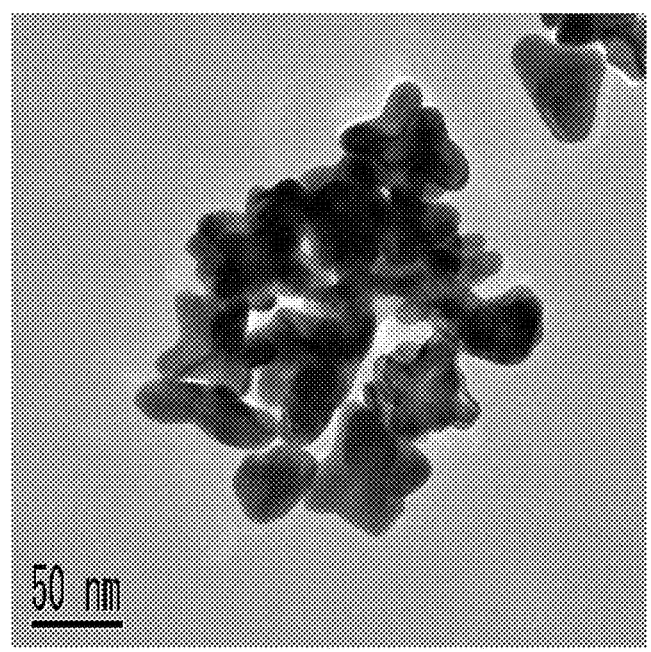
FIG. 2B is a transmission electron microscope image of one example of the blue-colored gold nanoparticles of the present invention after growth.
Figure 3A:
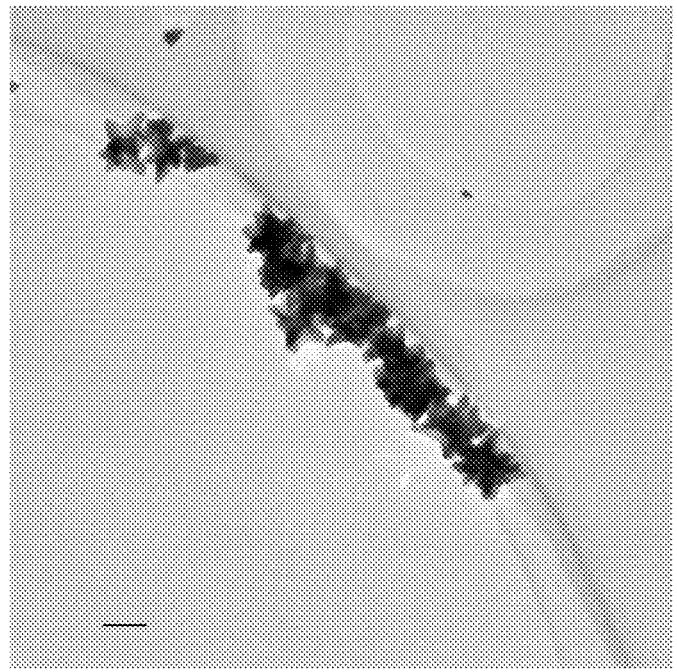
FIG. 3A is a transmission electron microscope image showing another example of the blue-colored gold nanoparticles of the present invention before growth at 20-fold magnification (the length of the scale bar in the drawing is 50 mm).
Figure 3B:
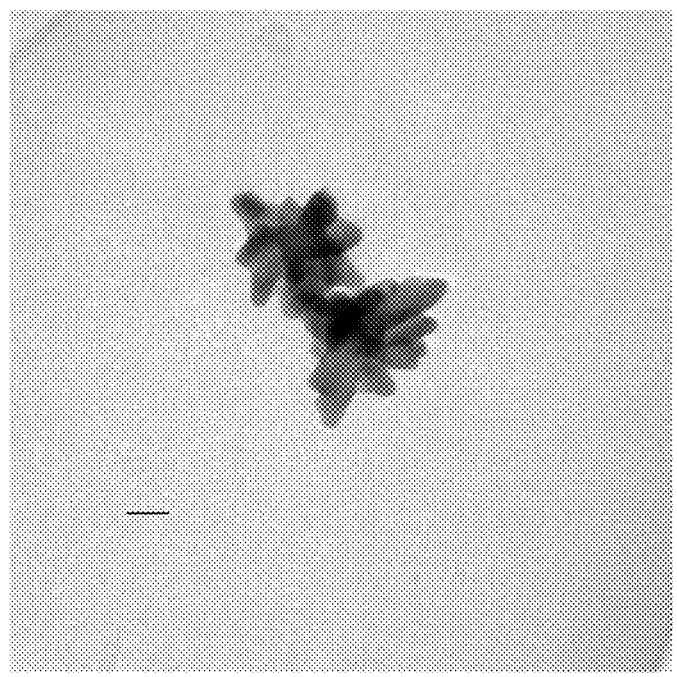
FIG. 3B is a transmission electron microscope image showing the blue-colored gold nanoparticles of FIG. 3A after growth at 50-fold magnification (the length of the scale bar in the drawing is 20 mm).

An example of increasing the particle size of the present invention without changing a peak wavelength is described specifically based on FIGS. 2A and 2B. In the absorption spectrum of "Particle 1" of FIG. 2A, the inventors of the present invention have achieved in the present invention the growth of the particle size into "Particle 2" of FIG. 2B without changing the peak wavelength of the ultraviolet visible absorption spectrum. In FIGS. 2A and 2B, the peak wavelength means a range from about 570 to 630 nm.

Examples of the first gold salt to be used in the nucleus formation stage of the present invention include salts such as chloroauric acid, gold tribromide, gold trifluoride, gold triiodide, gold tricyanide, gold monochloride, gold monoiodide, gold monofluoride, gold monocyanide, hydroxy gold oxide, gold trisnitrate, and gold nitrate, hydrates thereof, and a solution of gold in aqua regia. Gold salts are not limited to the above-mentioned ones but any substance capable of forming the first gold salt in an aqueous solution can be used.

As the first reducing agent to be used in the nucleus formation stage of the present invention, organic acid containing a piperazine ring which is a Good's buffer component can be used. Examples include, but not limited to, 2-[4-(2-hydroxyethyl)-1-piperazinyl]ethanesulfonic acid (which will hereinafter be abbreviated as "HEPES"), 4-(2-hydroxyethyl)-1-piperazinepropanesulfonic acid (which will hereinafter be abbreviated as "HEPPS"), 4-(2-hydroxyethylpiperazine-1-(2-hydroxypropane-3-sulfonic acid) (which will hereinafter be abbreviated as "HEPPSO"), piperazine-1,4-bis(2-ethanesulfonic acid) (which will hereinafter be abbreviated as "PIPES"), 3-[4-(2-hydroxyethyl)-1-piperazinyl]propanesulfonic acid (which will hereinafter be abbreviated as "EPPS"), and piperazine-1,4-bis(2-hydroxy-3-propanesulfonic acid) (which will hereinafter be abbreviated as "POPSO"). As the reducing agent, HEPES, HEPPSO, and PIPES are preferable. As the reducing agent, HEPES is more preferable. A mixture of them may be used as needed.

As the second gold salt to be used in the growth stage of the present invention, the gold salts which are described as examples as the first gold salt to be used in the nucleus formation stage can be used. The second gold salt and the first gold salt may be the same or different. Chloroauric acid can be used preferably as the first gold salt and the second gold salt.

As the second reducing agent to be used in the growth stage of the present invention, organic acids having reducing properties such as ascorbic acid and derivatives thereof, citric acid and derivatives thereof, α-hydroxycarboxylic acids such as D(L)-malic acid, D(L)-tartaric acid, tartronic acid, and mucic acid, lactic acid, tannic acid, and reducing sugar can be used. Of these, ascorbic acid and derivatives thereof and citric acid and derivatives thereof are preferred, of which ascorbic acid and derivatives thereof are most preferred. A mixture of them can also be used.

As the ascorbic acid and derivatives thereof, those having reducing properties such as ascorbic acid (salts thereof), isomers or analogues thereof, and derivatives thereof can be used. Examples include L (or D)-ascorbic acid, isoascorbic acid, erythorbic acid, scorbamic acid, dehydroisoascorbic acid, deoxyascorbic acid, halogenated deoxyascorbic acids such as chlorodeoxyascorbic acid, alkyl ester ascorbates such as ethyl ascorbate; alkali metal salts of ascorbic acid such as sodium ascorbate, and alkaline earth metal salts of ascorbic acid such as calcium ascorbate. Of these, L (or D)-ascorbic acid (salts thereof) and isoascorbic acid are particularly preferable. Mixtures of them can also be used as needed.

As citric acid and derivatives thereof, those having reducing properties such as citric acid (salts thereof), isomers or analogues thereof, and derivatives thereof can be used. Examples include citric acid, isocitric acid, citric anhydride, isocitric anhydride, alkali metal salts such as sodium citrate and potassium citrate, ammonium salts such as ammonium citrate, alkaline earth metal salts such as calcium citrate, and alkyl citrates such as methyl citrate and ethyl citrate. Of these, citric acid and sodium citrate are particularly preferable. Mixtures of them can also be used as needed.

The reaction temperature in the nucleus formation stage of the present invention is from 0 to 40° C., preferably from 10 to 30° C. (room temperature), more preferably from 15 to 25° C. The reaction is conducted from 30 minutes to 5 hours. The reaction temperatures exceeding 40° C. increase the number of spherical particles and reduce the yield. The reaction temperature reduced to even less than 0° C. does not increase the yield and is therefore technically useless, not economical, and wasteful.

The concentration of the first reducing agent to be used in the nucleus formation stage is from 1 to 150 mM, preferably from 30 to 100 mM in an aqueous solution in which the nucleus gold nanoparticles are formed in the nucleus formation stage. When concentrations are greater than 150 mM, the concentrations exceed the necessary concentration and become technically useless, uneconomical, and wasteful. When concentrations are less than 1 mM, the function of the reducing agent is too weak so that they are not sufficient for the nucleus formation reaction.

The concentration of the first gold salt to be used in the nucleus formation stage is from 0.1 to 100 mM, preferably from 1 to 50 mM and more preferably from 5 to 25 mM in an aqueous solution in which the nucleus gold nanoparticles are formed in the nucleus formation stage.

The term "mM" as used herein means mmol/L.

The reaction is conducted so that in the nucleus formation stage, the concentration of gold in the colloidal gold solution obtained by reacting the first reducing agent having the above-mentioned concentration range with the first gold salt having the above-mentioned concentration range falls within a range of from 0.1 to 100 mM.

The reaction temperature in the growth stage of the present invention is from 0 to 40° C., preferably from 10 to 30° C. (room temperature), more preferably from 15 to 25° C. The reaction is conducted for from 1 to 10 hours. At the reaction temperatures exceeding 40° C., the particles tend to become spherical ones, leading to a decrease in yield. At the same time, the maximum absorption wavelength of the ultraviolet visible absorption spectrum is below 570 nm and is thus shifted to a shorter wavelength side. The reaction temperatures reduced to be less than 0° C. have no effect and are useless.

Figure 4A:
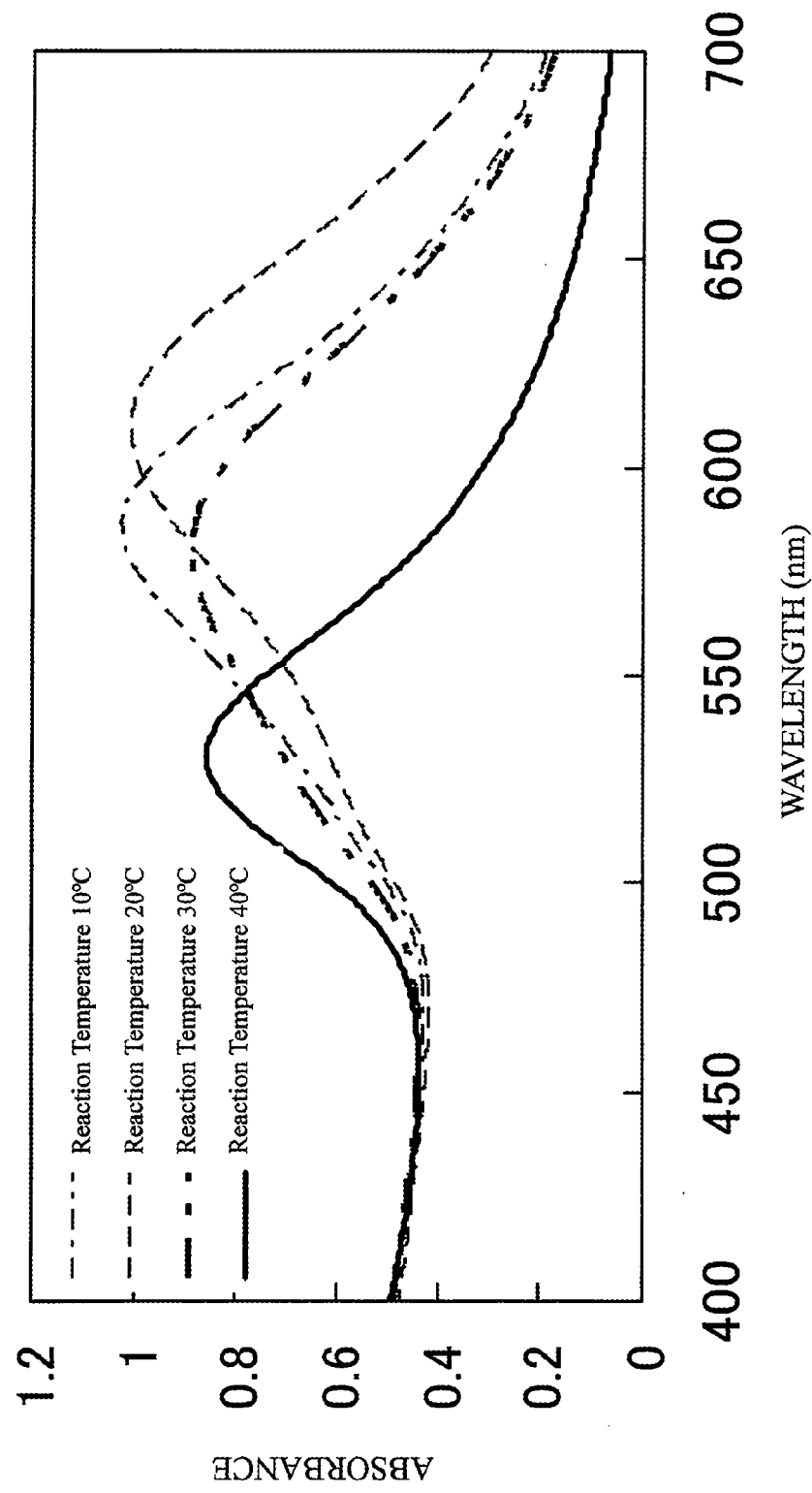
FIG. 4A shows the relationship between the wavelength (nm) of ultraviolet visible absorption spectrum and absorbance in the synthesis of the blue-colored gold nanoparticles of the present invention.
Figure 4B:
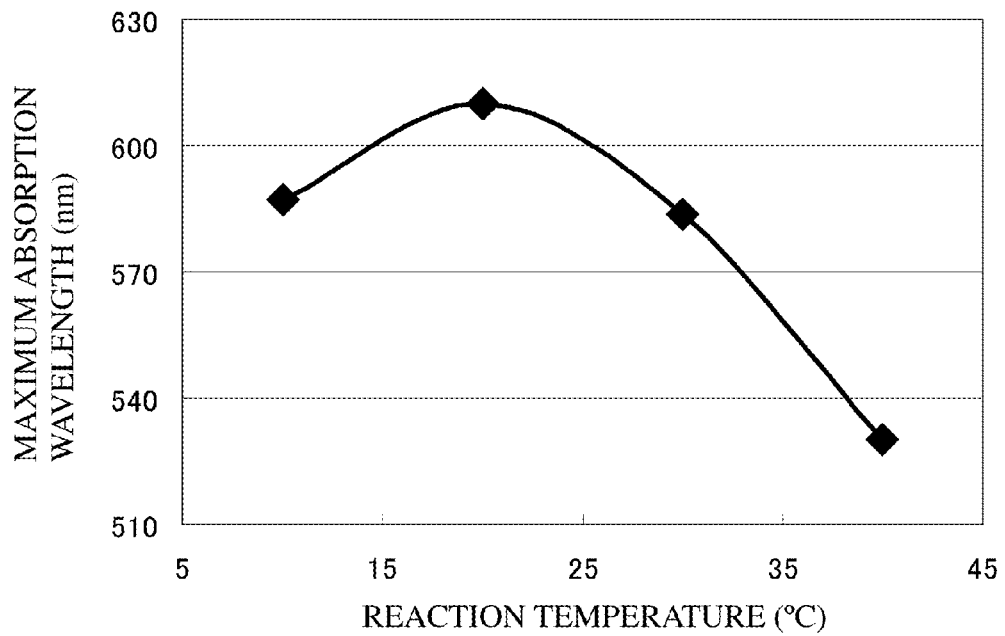
FIG. 4B shows the relationship between various reaction temperatures (° C.) and maximum absorption wavelength in the synthesis of the blue-colored gold nanoparticles of the present invention in FIG. 4A.

When a rational synthesis process of the gold nanoparticles of the present invention was extensively investigated with the standpoint of reducing the amount of unreduced chloroauric acid, the results will be described based on FIG. 4A and FIG. 4B. It has been found as a result of studying the relationship between the amount of the unreduced chloroauric acid and the reaction temperature or reaction rate that the nanoparticles show behavior to become more bluish by setting the reaction temperatures to be low temperatures. FIG. 4A and FIG. 4B have revealed that the reaction temperature set at from about 10 to 35° C. is most suitable.

Similarly, when explanation is described based on FIG. 4A and FIG. 4B., FIG. 4A shows the studying results of the wavelength (nm) at varied reaction temperatures: 10° C., 20° C., 30° C., and 40° C. When reaction temperatures are set at 40° C. or greater, a tendency to shift from a blue color to a red color can be observed. When the so-called reaction temperature is increased, the colloidal gold nanoparticles tend to be more reddish. On the other hand, when the reaction temperature is decreased, the colloidal gold nanoparticles tend to be more bluish. More specifically, as can be found from FIG. 4B, most colloidal gold particles having a maximum absorption wavelength of about 600 nm can easily be obtained by setting the reaction temperature at from about 10 to 30° C., most suitably from 15 to 25° C.

The concentration of the second reducing agent such as ascorbic acid or derivative thereof to be used in the growth stage of the present invention can be set at from 0.01 to 100 mM, preferably from 1 to 50 mM and more preferably from 5 to 25 mM in an aqueous solution in which the nucleus gold nanoparticles are grown in the growth stage.

Figure 5:
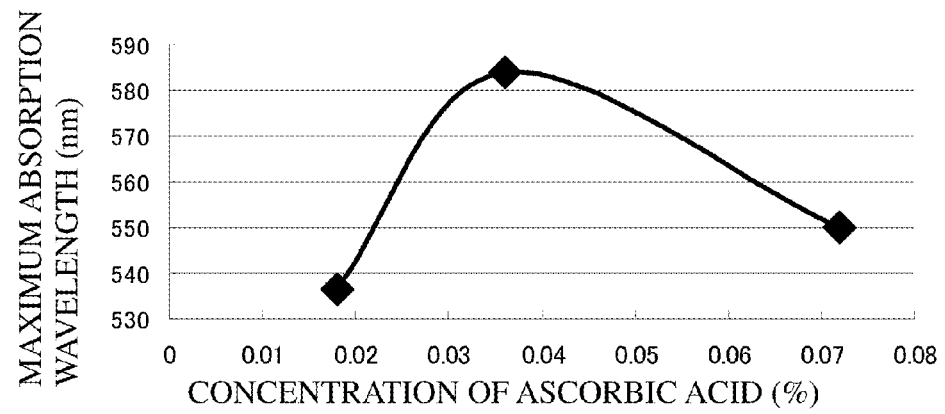
FIG. 5 shows the relationship between the maximum absorption wavelength (nm) of ultraviolet visible absorption spectrum and the concentration of ascorbic acid in the synthesis of the blue-colored gold nanoparticles of the present invention.

FIG. 5 shows the measurement results of a change in the maximum absorption wavelength of ultraviolet visible absorption spectrum of the colloidal gold particle suspensions obtained by changing the using amount of ascorbic acid in the growth stage as described in Example 4. The weight concentration of the aqueous solution of ascorbic acid added in the growth stage is plotted along the abscissa of FIG. 5. With consideration of the most suited amount of ascorbic acid or derivative thereof in the growth stage, it has revealed that as shown in FIG. 5, the aqueous solution of ascorbic acid to be added can be used at a relatively wide concentration range of from 0.02 to 0.07 (mass %) in order to develop the blue color of colloidal gold. However, from the standpoint of the relationship with blue color wavelength, the most suited condition of concentration of ascorbic acid in the whole aqueous solution in which nucleus gold nanoparticles are grown in the growth stage is from 0.075 to 0.15 mM. According to the finding of the inventors of the present invention, this range is technically critical.

The second gold salt to be used in the growth stage of the present invention can be used at a concentration of from 0.1 to 100 mM, preferably from 0.2 mM to 20 mM in an aqueous solution in which nucleus gold nanoparticles are grown in the growth stage.

The second reducing agent to be used in the growth stage of the present invention can be added in an amount of from 5 to 500 times, more preferably from 25 to 250 times per mole concentration of the nucleus gold nanoparticles added. The second gold salt to be used in the growth stage of the present invention is added in an amount of from 0.1 to 10 times, more preferably from 0.5 to 5 times per mole concentration of the nucleus gold nanoparticles added.

The second gold salt and the second reducing agent are simultaneously added dropwise to the colloidal gold solution, which has been synthesized in the nucleus growth stage, at a rate of from 0.1 to 3.0 ml/min, preferably from 0.3 to 1.5 ml/min, and particularly preferably from 0.5 to 1.0 mL/min.

The immunological measurement method according to the present invention is a measurement method based on an immunologically specific binding reaction derived from the affinity which a biological molecule has. For example, immunostaining, agglutination, ELISA, and immunochromatography are known. As such binding derived from affinity, antigen-antibody binding is typical and is used widely in the immunological measurement method. Not only such binding, but also sugar-lectin binding, hormone-receptor binding, enzyme-inhibitor binding, nucleic acid-complementary nucleic acid binding, or binding of nucleic acid and protein having a binding ability thereto can also be used. As immune response or immunological reaction, usable are, for example, a sandwich assay in which a sandwich type composite, for example, "solid-phase antibody-antigen-labeled antibody (labeling reagent)" is formed to trap and detect the antigen or a competitive assay using, as a principle, a competitive reaction of a solid-phased antigen and a free antigen in a specimen to a predetermined amount of a labeled antibody (labeling reagent) added into the reaction system. Of these, a most convenient assay making use of a sandwich reaction between an antigen and an antibody is an immunochromatographic assay using chromatography. Immunochromatographic assay is used generally because its operation is easy, needs only short detection time, and facilitates visual judgment.

Excellence of the blue-colored gold nanoparticles of the present invention in detection sensitivity when it is used for various immunochromatographic reagents is described based on FIG. 6. FIG. 6 shows the measurement results of color intensity by using an immunochromatographic reader in a test similar to immunochromatographic detection of Influenza B virus as described in Example 8. "Particle 1" is a system using, as a labeling substance, a blue-colored colloidal gold particle suspension formed only by the nucleus formation stage of Example 1 and "Particle 2" is a system using, as a labeling substance, a blue-colored colloidal gold particle suspension formed by the nucleus formation stage and the growth stage of Example 1. As an antigen, an aqueous solution containing 60 μg/ml of an antigen was used after dilution to 1400 times in case of "Particle 1" and after dilution to 2400 times in case of "Particle 2", respectively. When "Particle 1" (antigen dilution ratio: 1400 times) and "Particle 2" (antigen dilution ratio: 2400 times) are compared, it has revealed that color is vivid in "Particle 2", which is presumed to occur since the surface area of "Particle 2" is wider. It is impossible to identify the exact reason because there are various reasons. However, the blue-colored gold nanoparticles of the present invention are excellent in detection sensitivity and have an effect of markedly improving the accuracy of visual judgment using an immunochromatographic reagent.

In the immunological measurement method of the present invention, a sample (specimen) containing a detection object is, for example, mainly a biological sample such as blood, serum, plasma, urea, saliva, spinal fluid, sweat, tear, amniotic fluid, discharge from the nipple, nasal discharge, sputum, swab from the nasal cavity or pharynx, skin exudate, and extract from the tissue, cell, or feces.

The detection object in the present invention is not particularly limited as long as there is a substance specifically binding to it, for example, a substance specifically binding as in a reaction between an antigen and antibody or a nucleic acid and a nucleic acid complementary thereto or as long as such a substance can be prepared. The detection object may be a complete antigen which itself has antigenicity or may be a hapten (incomplete antigen) which itself has no antigenicity but can have antigenicity by the chemical modification. It is only necessary that a substance specifically binding to the detection object exists or can be prepared. It may be a monoclonal antibody or a polyclonal antibody.

Examples of the detection object in the present invention include peptide hormones (growth hormone (GH), adrenocorticotropic hormone (ACTH), melanocyte stimulating hormone (MSH), prolactin, thyroid stimulating hormone (TSH), luteinizing hormone (LH), follicle-stimulating hormone (FSH), pituitary hormone, calcium metabolism regulating hormone, renal hormone, gut hormone, vasoactive hormone, placental hormones such as human chorionic gonadotropin hormone (hCG), prostatic acid phosphatase (PAP), prostate specific antigen (PSA), alkali phosphatase, transaminase, trypsin, pepsinogen, α-fetoprotein (AFP), tumor specific substances such as carcinoembryonic antigen (CEA), serum protein components such as immunoglobulin G (IgG), rheumatism factors, serotonin, Urokinase, ferritin, substance P, estrogens such as estrone, fecal occult blood, syphilitic antibody, influenza virus, adenovirus, RS virus, rotavirus, HBs antigen, HBs antibody, bacterial antigens such as chlamydial antigen and *Streptococcus pyogens* antigen, natural or synthetic progestational hormone, androgens such as testosterone, adrenocortical hormones such as cortisol, cholesterol, bile acid, cardiotonic steroid and the other steroids such as sapogenin, epinephrine, dopamine, physiologically active alkaloids, amino-containing psychotropic agents, low molecular weight peptides such as TRH, thyroid hormones such as diiodothyronine, prostaglandins, vitamins, antibiotics such as penicillin, DNA, RNA, oligonucleotide, polynucleotide, amplified products thereof, other in-vivo components, drugs to be administered in vivo and metabolites thereof, foods such as pork, beef, chicken, and egg, and food extracts containing them. Of these detection objects, viruses are preferable and influenza virus, adenovirus, and RS virus are more preferable.

The most suited specimen in the present invention is a nasal discharge, a swab from the nasal cavity or pharynx, or sputum. By diluting such a specimen with a developing solution in advance, an antigen (virus: mainly, influenza virus, adenovirus, RS virus) collected from respiratory disease patients can be detected exactly as a detection target.

The developing solution for immunochromatography to be used in the present invention is prepared typically by using water as a solvent and adding thereto a buffer, a salt, a blocking agent, and a nonionic surfactant. There is no particular limitation for the adding order and they may be added simultaneously. When the developing solution is used, a mixture of a sample to be detected (target sample) and the developing solution may be supplied/added dropwise onto a sample pad (sample addition portion) for developing. Depending on the sample, the sample to be detected may be supplied/added dropwise onto a sample pad (sample addition portion) at first, followed by supply/dropwise addition of the developing solution onto the sample pad (sample addition portion) to develop the sample.

The buffer to be used for the immunochromatographic developing solution in the present invention is not particularly limited as long as it has action (buffer action) which is not influenced fatally by a change in the concentration due to the addition of the sample, evaporation or dilution of the sample, or mixing of some foreign maters from the outside.

Examples of the buffer in the present invention include good buffers such as acetate buffer (acetic acid+sodium acetate), phosphate buffer (phosphoric acid+sodium phosphate), citrate buffer (citric acid+sodium citrate), borate buffer, tris HCL buffer (tris(hydroxylmethyl)aminomethane+hydrochloric acid), TE buffer (tris+ethylenediaminetetraacetic acid), TAE buffer (tris+acetic acid+ethylenediaminetetraacetic acid), TBE buffer (tris+boric acid+ethylenediaminetetraacetic acid), and HEPES buffer (2-[4-(2-hydroxyethyl)-1-piperazinyl]ethanesulfonic acid). Of these, acetate buffer, phosphate buffer, and tris HCl buffer are preferable and tris HCl buffer are more preferable.

The salt to be used for the immunochromatographic developing solution of the present invention is not particularly limited as long as it is a salt obtained by a reaction between an acid and a base. Examples include sodium chloride and potassium chloride. Of these, sodium chloride is preferable.

Examples of the nonionic surfactant to be used for the immunochromatographic developing solution of the present invention include polyoxyethylene alkyl ethers, polyoxyethylene/polyoxypropylene alkyl ethers, polyoxyethylene sorbitan fatty acid esters ("Tween" series, trade name, product of Sigma Aldrich), polyoxyethylene p-t-octylphenyl ethers ("Triton" series, trade name; product of Sigma Aldrich), polyoxyethylene p-t-nonylphenyl ethers ("Triton N" series, trade name; product of Sigma Aldrich), alkyl polyglycosides, fatty acid diethanolamides, and alkyl monoglyceryl ethers etc. These nonionic surfactants may be used either singly or as a mixture of two or more of them.

It is possible and effective to incorporate, in the immunochromatographic developing solution of the present invention, one or more additives known to suppress a side reaction due to biological affinity or suppress a nonspecific reaction, for example, as an accelerator of an antigen antibody reaction or a blocking agent for repressing a non-specific reaction, proteins (such as bovine serum albumin, gelatin, and casein), high molecular compounds (such as polyethylene glycol, methyl cellulose, polyvinylpyrrolidone, polyvinyl alcohol, and dextran), ionic surfactants or polyanions (such as dextran sulfuric acid, heparin, polystyrene sulfonic acid, and chondroitin sulfuric acid), or antibiotics. Incorporation of them does not interfere with the effects of the present invention. It is also possible and effective to retain, on a transfer pathway of a mobile phase on a chromatographic medium constituting a stationary phase, one or more of proteins, high molecular compounds, ionic surfactants or polyanions, or antibiotics for accelerating an antigen antibody reaction or repressing a non-specific reaction. Retention of them does not interfere with the effects of the present invention.

In an immunochromatographic device for detecting a detection target in a specimen, the structure and operation/detection method of it are known. It usually comprises (1) a sample addition site, (2) a labeling substance retention site, (3) a chromatographic medium, (4) a detection site (which is also called "judgment portion"), (5) an absorption site, and (6) a backing sheet.

A specimen sample obtained by diluting a specimen in advance is added dropwise by using a developing solution to a sample pad of a conventional immunochromatographic device and developed on an immunochromatographic medium in the direction of an absorption site to cause an antigen-antibody reaction. Based on this reaction, assay such as identification, determination, or the like of a detection target in the specimen can be conducted.

The immunochromatographic device will be described.

The sample addition site (1) is made of a porous sheet such as glass filter paper which permits rapid absorption of a sample but has a weak retention power so that it enables prompt transfer of the sample to a reaction site.

The labeling substance retention site (2) retains a labeling reagent obtained by labeling a reagent component with a labeling component. Examples of the labeling component include colloidal metal particles, latex particles, enzymes, and fluorescent compounds. Of these, colloidal metal particles are most suitable. The colloidal particles of the blue-colored gold nanoparticles of the present invention are used as the labeling component. The reagent component is a particle or a molecule having an ability of recognizing an analyte, preferably a monoclonal antibody or a polyclonal antibody, or a fragment thereof (second reagent).

The chromatographic medium (3) has the detection site (4) on a membrane carrier. The membrane carrier is not particularly limited as long as it can absorb and transfer a sample specimen through capillary action. For example, it can be selected from the group consisting of nitrocellulose, cellulose acetate, nylons, polyether sulfone, polyvinyl alcohol, polyesters, glass fibers, polyolefins, and celluloses, and artificial polymers made of mixed fibers thereof.

At the detection site (4), a monoclonal antibody or a polyclonal antibody, or a fragment thereof (first reagent) is supported and fixed on a nitrocellulose sheet.

The absorption site (5) is made of a material having an ability to rapidly absorb an excess sample, for example, glass filter paper etc.

The backing sheet (6) is a base material. By applying or attaching an adhesive or an adhesive tape to one side of the sheet, the sheet has adhesiveness on one side and some or all of the sample addition site (1), the labeling substance retention site (2), the chromatographic medium (3), the detection site (4), and the absorption site (5) are adhered closely. The backing sheet (6) is not particularly limited as a base material as long as it is made impermeable or moisture impermeable to the sample solution by the adhesive.

Either one or both of the reagent component (first reagent) to be used for the detection site (4) and the reagent component (second reagent) to be used for the labeling reagent may be a monoclonal antibody or a polyclonal antibody. It is preferable that the reagent component (second reagent) to be used for the labeling reagent is a monoclonal antibody having high specificity from the standpoint of measurement sensitivity or the like. The reagent component (first reagent) to be used for the detection site (4) may be either a monoclonal antibody or a polyclonal antibody.

The monoclonal antibody or polyclonal antibody, or a fragment thereof is known and is available. It can be prepared in a known manner. Examples of antibody producing animals include human, mouse, rat, rabbit, goat etc. As an immunoglobulin, any of IgG, IgM, IgA, IgE, and IgD may be used.

The monoclonal antibody can be obtained by the conventional method. Splenic cells and myeloma cells of mice immunized with an antigen (for example, influenza A virus) are hybridized. A hybridoma that produces a target antibody is selected and a monoclonal antibody produced therefrom is obtained. Refer to, for example, the method announced by Köhler and Milstein (Nature, 256 (1975), 495-497).

The polyclonal antibody can be obtained in a usual manner by isolating a target antibody from an anti-serum obtained by immunizing a producing animal (such as human, mouse, rat, rabbit, goat, horse etc.) with an antigen (for example, influenza A virus).

Although it is described in Examples of the present invention that a mouse derived anti-influenza A monoclonal antibody is used as the reagent component (second reagent) to be used for the labeling reagent and a mouse anti-influenza A monoclonal antibody is used as the reagent component (first reagent) to be used for the detection site (4), the reagent components are not limited to them. A mouse derived anti-influenza A polyclonal antibody can also be used.

The following is the outline of the judgment principle.

1. A predetermined amount (usually from 0.1 to 2 ml) of a specimen sample (specimen diluted with a developing solution) is added dropwise onto the sample pad (1). When the specimen sample is added dropwise, it is absorbed quickly in the sample pad (1) but the resulting pad starts moving immediately together with the sample. When the sample pad (1) is impregnated with an immunochromatography reagent composition, the immunochromatography reagent composition is dissolved in the water content of the specimen sample and starts moving together with the specimen sample.

2. The specimen sample firstly moves to the labeling substance retention site (2). When the specimen sample passes through the site, the labeling reagent (second reagent) retained on the labeling substance retention site (2) is dissolved in the water of the sample and moves together with the sample.

3. Next, the labeling reagent dissolved in the water of the specimen sample passes through the detection site (4) on the chromatographic medium (3). Here, a non-specific binding reaction is suppressed by the immunochromatography reagent composition dissolved in the specimen sample. When the specimen sample contains a detection target (for example, antigen), specific reaction and binding occurs with being sandwiched between the antibody supported and fixed on the detection site (4) and the labeling reagent due to the antigen-antibody specific binding reaction, resulting in coloring of the detection site (4). When the specimen sample does not contain a detection target (for example, antigen), the labeling reagent dissolved in the water of the sample, even if the sample passes through the detection site (4) on the chromatographic medium (3), a specific binding reaction does not occur. Therefore, the detection site (4) is not colored.

4. Lastly, the water of the sample moves to the absorption site (5).

Thus, the presence or absence of a detection target (for example, an antigen) in the specimen sample can be exactly judged.

The present invention will hereinafter be described specifically by Examples and Comparative Examples. However, the present invention is not limited to or by these Examples.

(i) Measurement of Average Particle Size

Although an average particle size can be determined by gravimetric light scattering (determined from a precipitation rate of colloidal particles in a sol state rotated at from 14000 to 5530000×g and treated in an ultracentrifuge), in the present invention, the average particle size is calculated using dynamic light scattering (DLS) analyzer "Zetasizer Nano ZS" (trade name; product of Malvern Instruments). It is also possible to measure a projected area diameter of 100 particles selected randomly from a projection photograph taken by a transmission electron microscope (TEM, "JEM-2010", product of JEOL, Ltd.) and calculate, based on the average value, an average particle diameter (average particle size). An average nucleus size is calculated similarly from an average value of the projected area diameter of 100 particles selected randomly from a TEM projection photograph and an average protrusion length (average length of graft) is calculated by dividing a difference between the average particle size and the average nucleus size by 2.

Example 1

In this Example, confeito-shaped colloidal nucleus was formed by reducing chloroauric acid serving as the first gold salt with HEPES serving as the first reducing agent in the nucleus formation stage. Then, in the growth stage, chloroauric acid serving as the second gold salt and L-ascorbic acid serving as the second reducing agent were simultaneously added dropwise to form confeito-shaped colloidal gold having a particle size greater.

[Nucleus Formation Stage]

To a 10-ml glass container with a lid, 10 ml of $4\times10^{-2}$ mol/L HEPES pH 7.8 was charged and it was retained in a temperature-controlled bath until the liquid temperature became 25° C. Separately, 0.7 g ($1.6\times10^{-2}$ mol) of chloroauric acid tetrahydrate was dissolved in 100 ml of ultrapure water. The resulting solution was retained on ice until the liquid temperature became 4° C. When the liquid temperature of each of the aqueous solution of HEPES and the aqueous solution of chloroauric acid became stable, 0.3 ml of the aqueous solution of chloroauric acid was added dropwise to the aqueous solution of HEPES. The reaction mixture was allowed to stand for one hour in the 25° C. temperature-controlled bath. As a result, colloidal gold nanoparticles having an average particle size including the protrusion of about 43 nm and having a substantially confeito shape, graft shape, or multipod shape (having from 1 to 9 protrusions) were prepared. The yield per unit volume (0.1 ml) of the colloidal solution was about 91%. The residue is presumed to include spherical particles, unreacted particles, or the like.

[Growth Stage]

The colloidal nucleus (5 ml) prepared by the above-mentioned process and having a gold concentration of $4.0\times10^{-4}$ mol/L was charged in a 500 ml three-necked flask and stirred in a temperature-controlled bath until the liquid temperature became 20° C. After becoming the liquid temperature stable, an aqueous solution of chloroauric acid obtained by dissolving $1.5\times10^{-2}$ g ($4.0\times10^{-5}$ mol) of chloroauric acid tetrahydrate in 116 ml of ultrapure water and 116 ml of an aqueous solution of L-ascorbic acid obtained by dissolving $4.2\times10^{-2}$ g ($2.4\times10^{-4}$ mol) of L-ascorbic acid in 116 ml of ultrapure water were simultaneously added dropwise at a rate of 1.0 ml/min. They were reacted for 2 hours with stirring to conduct the growth stage. After completion of the dropwise addition, the three-necked flask was taken out from the temperature-controlled bath and allowed to stand overnight in a refrigerator. The gold nanoparticles thus obtained had an average particle size (DLS) of about 66.5 nm. TEM observation showed that gold nanoparticles had an average nucleus size of about 35.7 nm; an average protrusion length of 13.2 nm; four or more protrusions on average; a protrusion angle of about 50 degrees; and an AR of 1 or greater. The colloidal gold solution thus obtained was blue (measured visually based on the Munsell color system: hue of approximately 5B) and had a maximum absorption wavelength of 610 nm.

Example 2

This Example was conducted in order to synthesize confeito-shaped colloidal gold having a longer protrusion.

The colloidal nucleus (5 ml) formed in the nucleus formation stage of Example 1 and having a gold concentration of $4.0\times10^{-4}$ mol/L was charged in a 500 ml three-necked flask and stirred in a temperature-controlled bath until the liquid temperature became 20° C. After becoming the liquid temperature stable, an aqueous solution of chloroauric acid obtained by dissolving $1.5\times10^{-2}$ g ($4.0\times10^{-5}$ mol) of chloroauric acid tetrahydrate in 116 ml of ultrapure water and 116 ml of an aqueous solution of L-ascorbic acid and HEPES obtained by dissolving $4.2\times10^{-2}$ g ($2.4\times10^{-4}$ mol) of L-ascorbic acid and 0.11 g ($4.0\times10^{-3}$ mol) in 116 ml of water were simultaneously added dropwise at a rate of 1.0 ml/min. They were reacted for 2 hours with stirring. Thus, the growth stage was conducted. After completion of the dropwise addition, the three-necked flask was taken out from the temperature-controlled bath and allowed to stand overnight in a refrigerator.

The gold nanoparticles thus obtained had an average particle size (DLS) including the protrusion of about 98 nm. It was presumed from the results of TEM observation that a larger amount of confeito-shaped colloidal gold having a longer protrusion was formed. The confeito-shaped colloidal gold thus formed had an average nucleus size of about 65.7 nm, an average length of the protrusion (graft) thus grown of about 16.7 nm, 4 or more protrusions, a protrusion angle of about 50 degrees, and an AR of 1 or greater. The colloidal gold solution thus obtained was bluish green (measured visually based on the Munsell color system: hue of approximately 8BG) and had a maximum absorption wavelength of 641 nm.

Example 3

In a similar manner to Example 1 except that the liquid temperature in the growth stage was changed to 10° C., colloidal gold was synthesized. The maximum absorption wavelength of the colloidal gold solution thus obtained is shown in Table 1.

In a 500 ml three-necked flask, 5 ml of $4.3\times10^{-4}$ mol/L colloidal nucleus formed in the nucleus formation stage of Example 1 was charged, followed by stirring in a temperature-controlled bath until the growth temperature, namely, the liquid temperature became 10° C. After becoming the liquid temperature stable, an aqueous solution of chloroauric acid obtained by dissolving $1.7\times10^{-2}$ g ($4.2\times10^{-5}$ mol) of chloroauric acid tetrahydrate in 116 ml of ultrapure water and 116 ml of an aqueous solution of L-ascorbic acid obtained by dissolving $4.2\times10^{-2}$ g ($2.4\times10^{-4}$ mol) of L-ascorbic acid in 116 ml of water were simultaneously added dropwise at a rate of 1.0 ml/min. They were reacted for 2 hours with stirring. Thus, the growth stage was conducted. After completion of the dropwise addition, the three-necked flask was taken out from the temperature-controlled bath and allowed to stand overnight in a refrigerator.

The gold nanoparticles thus obtained had an average particle size (DLS), including the protrusion, of about 67 nm. TEM observation showed that the gold nanoparticles thus obtained had an average nucleus size of about 51.0 nm, an average length of the grown protrusion (graft) of about 8.0 nm, four or more protrusions, a protrusion angle of about 50 degrees, and an AR of 1 or greater. The colloidal gold solution thus obtained was blue (measured visually based on the Munsell color system: color hue of approximately 5PB) and had a maximum absorption wavelength of 587 nm.

Example 4

In a similar manner to Example 1 except that the liquid temperature in the growth stage was changed to 30° C., substantially confeito-shaped, graph-shaped, or multipod-shaped (with from 2 to 4 protrusions) colloidal gold nanoparticles having three-dimensional protrusions were synthesized.

The gold nanoparticles thus obtained had an average particle size (DLS), including the protrusion, of about 60.5 nm. TEM observation showed that the gold nanoparticles thus obtained had an average length of the grown protrusion (graft) of about 7.5 nm, four or more protrusions on average, a protrusion angle of about 50 degrees, and an AR of 1 or greater. The colloidal gold solution thus obtained had a maximum absorption wavelength of 586.5 nm.

The results are shown in Table 1.

Comparative Example 1

In a similar manner to Example 1 except the liquid temperature in the growth stage was changed to 40° C., colloidal gold was synthesized. The maximum absorption wavelength of the colloidal gold solution thus obtained is shown in Table 1.

The gold nanoparticles obtained by changing the temperature in the growth stage to 40° C. had an average particle size (DLS) including the protrusion of about 53 nm. TEM observation showed that the gold nanoparticles thus obtained had an average nucleus size of 45 nm, an average length of the grown protrusion (graft) of about 4 nm, four or more protrusions on average, and a protrusion angle of about 10 degrees. The colloidal gold particles thus obtained were multi-pod shaped (having from 2 to 4 protrusions) with slightly rounded three-dimensional protrusions. The remaining portion is presumed to contain spherical particles and unreacted particles. The colloidal gold solution thus obtained was reddish (measured visually based on the Munsell color system: hue of approximately 10RP) and had a maximum absorption wavelength of 530 nm.

Comparative Example 2

In a similar manner to Example 1 except that the amount of ascorbic acid in the growth stage was changed to $2.1 \times 10^{-2}$ g ($1.2 \times 10^{-4}$ mol), colloidal gold was synthesized. The maximum absorption wavelength of the colloidal gold solution thus obtained is shown in Table 1.

To a 500 ml three-necked flask, 5 ml of $4.3 \times 10^{-4}$ mol/L colloidal nucleus formed in the nucleus formation stage of Example 1 was charged, followed by stirring in a temperature-controlled bath until the growth temperature, namely, the liquid temperature became 30° C. When the liquid temperature became stable, an aqueous solution of chloroauric acid obtained by dissolving $1.7 \times 10^{-2}$ g ($4.2 \times 10^{-5}$ mol) of chloroauric acid tetrahydrate in 116 ml of ultrapure water and 116 ml of an aqueous solution of L-ascorbic acid obtained by dissolving $2.1 \times 10^{-2}$ g ($1.2 \times 10^{-4}$ mol) of L-ascorbic acid in 116 ml of ultrapure water were simultaneously added dropwise at a rate of 1.0 ml/min. They were reacted for 2 hours with stirring. Thus, the growth stage was conducted. After completion of the dropwise addition, the three-necked flask was taken out from the temperature-controlled bath and allowed to stand overnight in a refrigerator.

The gold nanoparticles thus obtained had an average particle size including the protrusion of about 48 nm.

The colloidal gold solution thus obtained had a maximum absorption wavelength of 536.3 nm and was reddish.

Comparative Example 3

In a similar manner to Example 1 except that the amount of ascorbic acid in the growth stage was changed to $8.4 \times 10^{-2}$ g ($4.8 \times 10^{-4}$ mol), colloidal gold was synthesized. The maximum absorption wavelength of the colloidal gold solution thus obtained is shown in Table 1.

The colloidal gold obtained by changing the growth stage temperature to 30° C. had an average nucleus diameter of 60.2 nm and an average particle size of 70.2 nm. The colloidal gold solution thus obtained had a maximum absorption wavelength of 550.0 nm and was orangish.

Example 5

In a similar manner to Example 2 except for the use of HEPPSO instead of HEPES, colloidal gold particles having an average particle size of about 72 nm were obtained. The colloidal gold solution thus obtained exhibited a blue color (measured visually based on the Munsell color system: hue of approximately 1B) and had a maximum absorption wavelength of 632 nm.

Example 6

In a similar manner to Example 2 except for the use of PIPES instead of HEPES, colloidal gold particles having an average particle size of about 81 nm were prepared. The colloidal gold solution thus obtained exhibited a blue color (measured visually based on the Munsell color system: hue of approximately 3B) and had a maximum absorption wavelength of 626 nm.

Example 7

In a similar manner to Example 2 except that ascorbic acid to be used in the growth stage was replaced by $4.7 \times 10^{-2}$ g ($2.4 \times 10^{-4}$ mol) of sodium L-ascorbate and HEPES was used in an amount of 0.22 g ($8.0 \times 10^{-3}$ mol), a colloidal gold solution was synthesized.

The colloidal gold particles thus obtained had an average particle size (DLS) including the protrusion of about 82 nm, an average nucleus size of about 48 nm, an average length of the protrusion (graft) thus grown of about 20 nm, four or more protrusions on average, a protrusion angle of about 50 degrees, and an AR of 1 or greater. The colloidal gold solution thus obtained was exhibited a dark blue color (measured visually based on the Munsell color system: hue of approximately 5PB) and had a slightly high maximum absorption wavelength of 752 nm.

Measurement results of Examples 1 to 7 and Comparative Examples 1 to 3 are shown collectively in Table 1.

TABLE 1

| | Liquid temperature in the growth stage (° C.) | Amount of L-ascorbic acid (or substitute) in the growth stage (g) | Amount of HEPES (or substitute) in the growth stage (g) | Maximum absorption wavelength (nm) |
|---|---|---|---|---|
| Example 1 | 20 | $4.2 \times 10^{-2}$ | 0 | 610 |
| Example 2 | 20 | $4.2 \times 10^{-2}$ | 0.11 | 641 |
| Example 3 | 10 | $4.2 \times 10^{-2}$ | 0 | 587 |
| Example 4 | 30 | $4.2 \times 10^{-2}$ | 0 | 586.5 |
| Example 5 | 20 | $4.2 \times 10^{-2}$ | (HEPPSO) 0.11 | 632 |
| Example 6 | 20 | $4.2 \times 10^{-2}$ | (PIPES) 0.11 | 626 |
| Example 7 | 20 | $4.7 \times 10^{-2}$ (LAANa) | 0.22 | 752 |
| Comp. Ex. 1 | 40 | $4.2 \times 10^{-2}$ | 0 | 530 |
| Comp. Ex. 2 | 30 | $2.1 \times 10^{-2}$ | 0 | 536.3 |
| Comp. Ex. 3 | 30 | $8.4 \times 10^{-2}$ | 0 | 550 |

LAANa in the above table means L-ascorbic acid.

A colloidal gold solution was synthesized in a similar manner to Example 1 except for the use of citric acid instead of ascorbic acid in the growth stage.

The colloidal gold particles thus obtained had an average particle size (DLS) including the protrusion and an average nucleus size on the same level as those of the colloidal gold particles obtained in each Example. They had an average length, average number, and an angle of the grown protrusion (graft) on the same level as those of the colloidal gold particles obtained in each Example. They had Ar of 1 or greater. Thus, the colloidal gold solution thus obtained was on the same level as that obtained in each Example. This suggests that an organic acid other than the organic acid having reducing properties such as ascorbic acid or derivative thereof, or citric acid or derivative thereof can be used as the second reducing agent to be used in the growth stage of the present invention. For example, it is presumed that a colloidal gold solution obtained using D(L)-malic acid, D(L)-tartaric acid, lactic acid, tannic acid, or reducing sugar has properties within a predetermined range satisfying the object of the present invention, although there is a little different from the colloidal gold solution obtained according to the present invention. A predetermined colloidal gold solution can be obtained according to the above-mentioned method such as that described in Example 7 by using an inorganic or organic salt of each of the above-mentioned acids.

Although the effectiveness of the present invention will hereinafter be described by Tests, the present invention is not limited to or by it.

<Test of Virus Detection by Immunochromatography>

Example 8

1. Preparation of Reaction Site on Chromatographic Medium

Anti-influenza A virus monoclonal antibody diluted to the concentration of 1.0 mg/mL with a phosphate buffer (pH 7.4) containing 5 wt % isopropyl alcohol was applied to the developing direction upstream side (Table 2: line 1) of a nitrocellulose membrane ("HF120"; product of Millipore) and an anti-influenza B virus monoclonal antibody was applied to the downstream side (Table 2: line 2) of the anti-influenza A monoclonal antibody by using an antibody applicator (product of BioDot), followed by drying at 50° C. for 30 minutes. After drying, it was dried overnight at room temperature and a reaction site was prepared on a chromatographic medium.

2. Preparation of Labeling Substance Solution 1

To 0.5 mL of the blue colloidal gold suspension obtained in Example 1, 0.1 mL of an anti-influenza B virus monoclonal antibody diluted to a concentration of 0.1 mg/mL with a phosphate buffer (pH 7.4) was added and the resulting mixture was allowed to stand at room temperature for 10 minutes. Then, 0.1 mL of a phosphate buffer (pH 7.4) containing a 10 wt % bovine serum albumin was added. After thorough stirring, the reaction mixture was centrifuged at 8000×g for 15 minutes. The supernatant was removed and then, 0.1 mL of a phosphate buffer (pH 7.4) containing 1 wt % bovine serum albumin was added to obtain Labeling substance solution 1.

3. Preparation of Labeling Substance Solution 2

To 0.5 mL of a colloidal gold suspension "LC-40" (product of Tanaka Kikinzoku Kogyo: average particle size of 40 nm) was added 0.1 mL of an anti-influenza A virus monoclonal antibody diluted to a concentration of 0.1 mg/mL with a phosphate buffer (pH 7.4) and the resulting mixture was allowed to stand at room temperature for 10 minutes. Then, 0.1 mL of a phosphate buffer (pH 7.4) containing a 10 wt % bovine serum albumin was added. After thorough stirring, the reaction mixture was centrifuged at 8000×g for 15 minutes. The supernatant was removed and then, 0.1 mL of a phosphate buffer (pH 7.4) containing 1 wt % bovine serum albumin was added to obtain Labeling substance solution 2.

4. Preparation of Chromatographic Medium

Labeling substance solutions 1 and 2 prepared above were added uniformly to a pad made of glass fibers and then, dried in a vacuum drier to obtain a detection reagent retention member. Then, the chromatographic medium thus prepared, the detection reagent retention member, a sample pad to be used for a sample addition portion, and an absorption pad for absorbing the developed sample and insoluble carrier were laminated on a base material made of a backing sheet. Finally, the laminate was cut into a chromatographic medium having a width of 5 mm.

5. Measurement

By using the chromatographic medium thus prepared, presence or absence of Influenza A virus (Table 2: antigen A) and Influenza B virus (Table 2: antigen B) in a sample was analyzed by the following method. Namely, a developing solution composed of 0.5% Tween 20, 0.6% polyvinylpyrrolidone (PVP) K-90 (molecular weight: 360000), and tris buffer solution (pH 8.0) containing 1.0% bovine serum albumin and 150 mM sodium chloride was used as a negative specimen sample. To the resulting developing solution, inactivated Influenza A virus and/or Influenza B virus having a protein concentration of 25 ng/mL was added to obtain a positive specimen sample. The negative specimen sample and the positive specimen sample, each 150 μL, were placed and developed on the sample pad of the chromatographic medium. Fifteen minutes later, visual judgment was conducted. The specimen sample from which a luminescence signal was clearly found from the test lines (lines 1 and 2) at the reaction sites was rated as "+"; the specimen sample from which a luminescence signal was found, though it had a very pale color was rated as "±"; and the specimen sample from which no luminescence signal was found was rated as "−". The results of Example 5 are shown in Table 2.

TABLE 2

| | Negative specimen | | Antigen A + Antigen B | | Only Antigen A | | Only Antigen B | |
|---|---|---|---|---|---|---|---|---|
| Line 1 | − | None | + | Red | + | Red | − | None |
| Line 2 | − | None | + | Blue | − | None | + | Blue |

By using the confeito-shaped colloidal gold particles of the present invention in combination with conventionally used colloidal metal particles such as spherical colloidal gold particles as a labeling agent for immunological assay, particularly, immunochromatographic assay, two different detection targets contained in a biological sample were detected clearly with high sensitivity as luminescence signals from the test lines (lines 1 and 2) at the reaction sites, respectively, without misidentification.

INDUSTRIAL APPLICABILITY

Colloidal gold particles of the present invention exhibit a blue color, have no toxicity because they do not contain a protective colloid forming agent or ammonium salt, and contain gold good for health. Therefore, they can be used as pigments, cosmetics, labeling agents for immunological measurement, cytochemical markers, or protein staining agents. In particular, the above-mentioned colloidal gold particles characterized by:
(1) having from 4 to 20 protrusions on a spherical nucleus of the colloidal gold particles, and
(2) having an average particle size of from 20 to 200 nm, and capable of labeling and distinguishing a detection target by a visible blue color can be used as a labeling agent for immunological measurement in an immunochromatography test having two or more color lines.

Although the present invention is described in detail or referring to some specific embodiments, it is apparent for those skilled in the art that various changes or modifications can be given without departing from the scope of the present invention.

The present application is based on Japanese Patent Application (Japanese Patent Application No. 2010-248463) filed on Nov. 5, 2010 and the content of which is incorporated herein by reference. All the references cited are incorporated herein as a whole.

The invention claimed is:

1. A plurality of blue-colored gold nanoparticles having an average particle nucleus size of from 20 to 60 nm, an average particle size of from 60 to 120 nm, four or more protrusions per nucleus, and a protrusion length of from 5 to 50 nm.

2. The blue-colored gold nanoparticles according to claim 1, wherein the maximum absorption wavelength in ultraviolet visible absorption spectra falls within a range of from 570 to 800 nm.

3. The blue-colored gold nanoparticles according to claim 1, wherein the gold nanoparticles are graft-shaped particles, multipod-shaped particles, or confeito-shaped particles having a three-dimensional protrusion.

4. The blue-colored gold nanoparticles according to claim 1, obtained by growing the periphery of the nucleus composed of gold nanoparticles.

5. A colloidal solution of blue-colored gold nanoparticles, comprising the blue-colored gold nanoparticles as described in claim 1; organic acid containing a piperazine ring which is a Good's buffer component; and an organic acid having reducing properties and is dispersed as a colloidal solution.

6. A labeling substance for immunological measurement comprising at least two kinds of blue-colored gold nanoparticles as described in claim 1 that differ in shape.

7. The labeling substance for immunological measurement according to claim 6, which comprises at least two kinds of gold nanoparticles of different shapes which are spherical gold nanoparticles and graft-shaped, multipod-shaped, or confeito-shaped gold nanoparticles having a three-dimensional protrusion.

8. An immunological measurement method using the blue-colored gold nanoparticles as described in claim 1 as a labeling substance comprising the steps of: combining an antibody-bound to one or more of the plurality of blue colored nanoparticles according to claim 1 with a sample containing a detection object, wherein the antibody binds specifically to the detection object to form a complex comprising the detection object and the antibody-bound one or more of the plurality of blue colored nanoparticles according claim 1; measuring a luminescent signal from the complex.

9. A method for producing blue-colored gold nanoparticles having an average particle size of 60 to 120 nm, comprising a nucleus formation step by reacting organic acid containing a piperazine ring which is a Good's buffer component with a solution of a first gold salt to form nucleus gold nanoparticles and a growth step by simultaneously adding and reacting a solution of a second gold salt and an organic acid having reducing properties with a solution of the nucleus gold nanoparticle to grow the nucleus gold nanoparticles.

10. The method for producing blue-colored gold nanoparticles according to claim 9, wherein the growth step is conducted at a reaction temperature of 10° C. or greater and less than 40° C.

11. The method for producing blue-colored gold nanoparticles according to claim 9, wherein the organic acid in the growth step has a concentration of from 0.075 to 0.15 mM.

12. The method for producing blue-colored gold nanoparticles according to claim 11, wherein the organic acid containing piperazine ring which is a Good's buffer component is one or more organic acids selected from the group consisting of 2-[4-(2-hydroxyethyl)-1-piperazinyl]ethanesulfonic acid, 4-(2-hydroxyethyl)-1-piperazinepropanesulfonic acid, 4-(2-hydroxyethyl)piperazine-1-(2-hydroxypropane-3-sulfonic acid), piperazine-1,4-bis(2-ethanesulfonic acid), 3-[4-(2-hydroxyethyl)-1-piperazinyl]propanesulfonic acid, and piperazine-1,4-bis(2-hydroxy-3-propanesulfonic acid).

13. The method for producing blue-colored gold nanoparticles according to claim 9, wherein the organic acid having reducing properties is one or more organic acids selected from the group consisting of tartaric acid, tartrates, tannic acid, tannates, ascorbic acid, ascorbates, citric acid, and citrates.

14. The method for producing blue-colored gold nanoparticles according to claim 9, wherein in the growth step, the organic acid containing a piperazine ring which is a Good's buffer component is used in combination with the organic acid having reducing properties.

* * * * *